United States Patent
Tabaru et al.

(10) Patent No.: US 9,439,620 B2
(45) Date of Patent: Sep. 13, 2016

(54) ULTRASOUND DIAGNOSIS APPARATUS

(75) Inventors: Marie Tabaru, Tokyo (JP); Takashi Azuma, Tokyo (JP); Hideki Yoshikawa, Tokyo (JP); Kunio Hashiba, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 421 days.

(21) Appl. No.: 13/992,083

(22) PCT Filed: Dec. 1, 2011

(86) PCT No.: PCT/JP2011/077853
§ 371 (c)(1),
(2), (4) Date: Jul. 17, 2013

(87) PCT Pub. No.: WO2012/077579
PCT Pub. Date: Jun. 14, 2012

(65) Prior Publication Data
US 2013/0289402 A1    Oct. 31, 2013

(30) Foreign Application Priority Data

Dec. 8, 2010  (JP) ................................ 2010-273565

(51) Int. Cl.
*A61B 8/00* (2006.01)
*A61B 8/08* (2006.01)
*G01S 7/52* (2006.01)

(52) U.S. Cl.
CPC ............... *A61B 8/08* (2013.01); *A61B 8/485* (2013.01); *G01S 7/52049* (2013.01); *A61B 8/0825* (2013.01); *A61B 8/0891* (2013.01); *G01S 7/52071* (2013.01); *G01S 7/52073* (2013.01)

(58) Field of Classification Search
CPC ...... A61B 8/08; A61B 8/485; A61B 8/0891; A61B 8/0825; G01S 7/52049; G01S 7/52073; G01S 7/52071

USPC .................................................. 600/437–469
See application file for complete search history.

(56) References Cited

U.S. PATENT DOCUMENTS

| 6,770,033 B1 * | 8/2004 | Fink ........................ A61B 8/08 600/443 |
| 8,150,128 B2 * | 4/2012 | Konofagou ............... A61B 8/08 382/131 |
| 9,302,124 B2 * | 4/2016 | Konofagou ............... A61N 7/00 |
| 2002/0010398 A1 * | 1/2002 | Bonnefous ................ A61B 8/08 600/442 |
| 2004/0068184 A1 * | 4/2004 | Trahey ..................... A61B 8/08 600/437 |

(Continued)

FOREIGN PATENT DOCUMENTS

| JP | 2002-538911 | 11/2002 |
| JP | 2003-530941 | 10/2003 |

(Continued)

OTHER PUBLICATIONS

International Search Report, International Application No. PCT/JP2011/077853, Filed Dec. 1, 2011, Mailed Jan. 31, 2012, ISA/Japanese Patent Office.
Deffieux et al., IEEE Trans Medical Imaging, vol. 28, No. 3, 2009.
Chen et al., IEE Trans. Ultrason. Ferro. Freq. Contr., vol. 56, No. 1, 2009.

(Continued)

*Primary Examiner* — Sanjay Cattungal
(74) *Attorney, Agent, or Firm* — Brundidge & Stanger, P.C.

(57) ABSTRACT

When multiple tissues having differing speeds of sound are intermixed in the viewing field of a measured subject such as a living body, the invention measures hardness, such as modulus of elasticity or viscosity, with high precision.

9 Claims, 19 Drawing Sheets

(56) References Cited

U.S. PATENT DOCUMENTS

| | | | |
|---|---|---|---|
| 2008/0097211 A1* | 4/2008 | Sarvazyan | A61B 8/0875 600/449 |
| 2008/0249408 A1* | 10/2008 | Palmeri | A61B 8/08 600/438 |
| 2009/0124901 A1* | 5/2009 | Fink | A61B 8/0825 600/437 |
| 2010/0069751 A1 | 3/2010 | Hazard et al. | |
| 2010/0191113 A1 | 7/2010 | Hazard et al. | |
| 2010/0280373 A1 | 11/2010 | Fan et al. | |
| 2010/0286520 A1* | 11/2010 | Hazard | A61B 8/06 600/439 |
| 2011/0130660 A1* | 6/2011 | Cloutier | A61B 5/02007 600/438 |
| 2013/0058195 A1* | 3/2013 | Cloutier | A61B 8/0825 367/99 |
| 2013/0091543 A1* | 4/2013 | Wade | G06F 21/54 726/1 |
| 2013/0139240 A1* | 5/2013 | Sawayanagi | G06F 21/41 726/8 |
| 2014/0094702 A1* | 4/2014 | Kim | G01N 29/0654 600/438 |
| 2015/0365407 A1* | 12/2015 | Jagana | H04W 12/12 726/29 |

FOREIGN PATENT DOCUMENTS

| | | |
|---|---|---|
| JP | 2008-534198 | 8/2008 |
| JP | 2010-069295 | 4/2010 |
| JP | 2010-172699 | 8/2010 |
| JP | 2010-259806 | 11/2010 |

OTHER PUBLICATIONS

Marie Tahara et al., "Choonpa Hosharyoku ni yoru Danseiritzu Keisoku", Report of the 2010 Spring Meeting, the Acoustical Society of Japan CD-ROM, Mar. 2010, pp. 1279 to 1280.

\* cited by examiner

FIG. 3
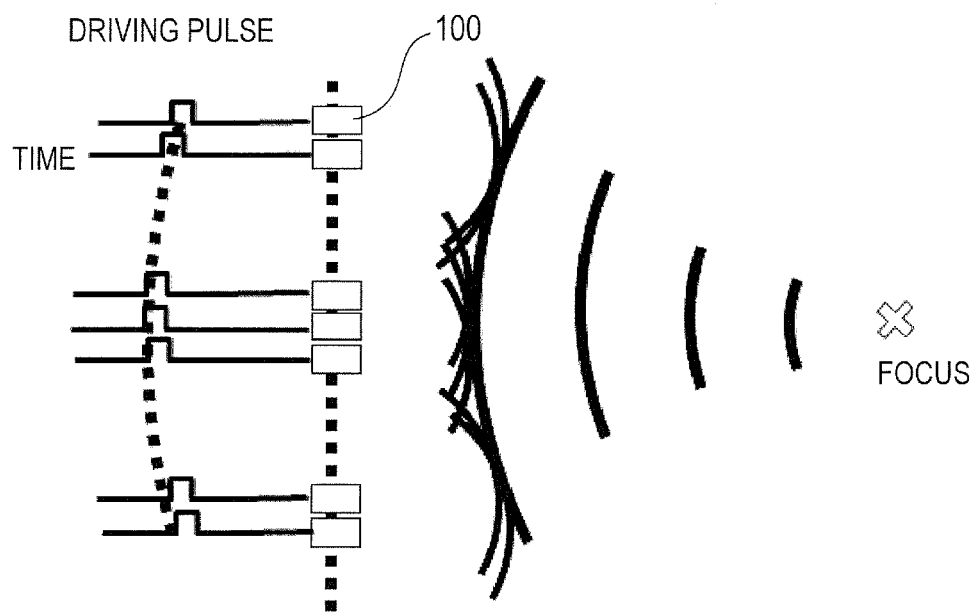
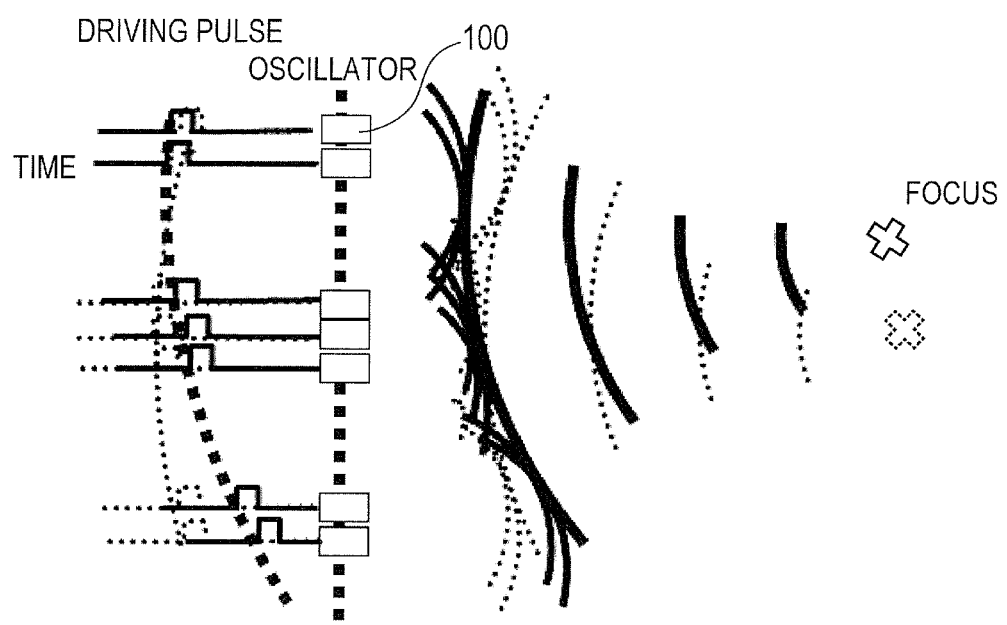

FIG. 9
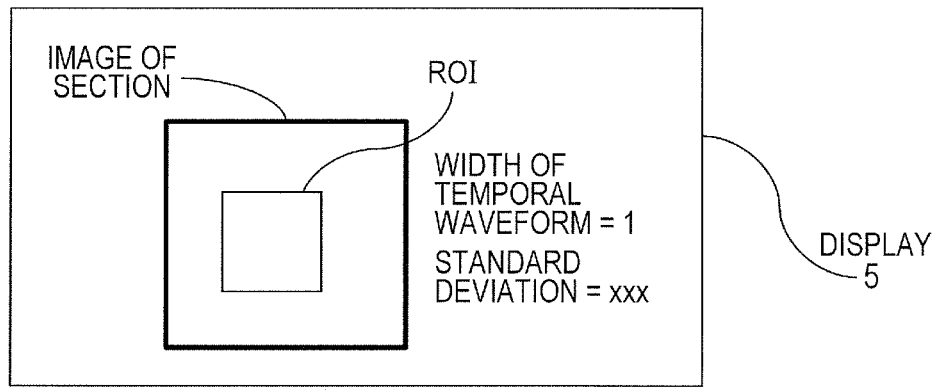
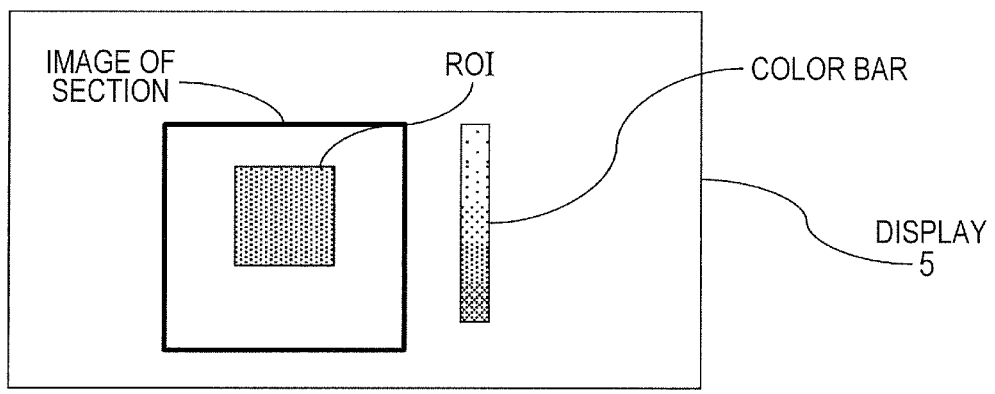
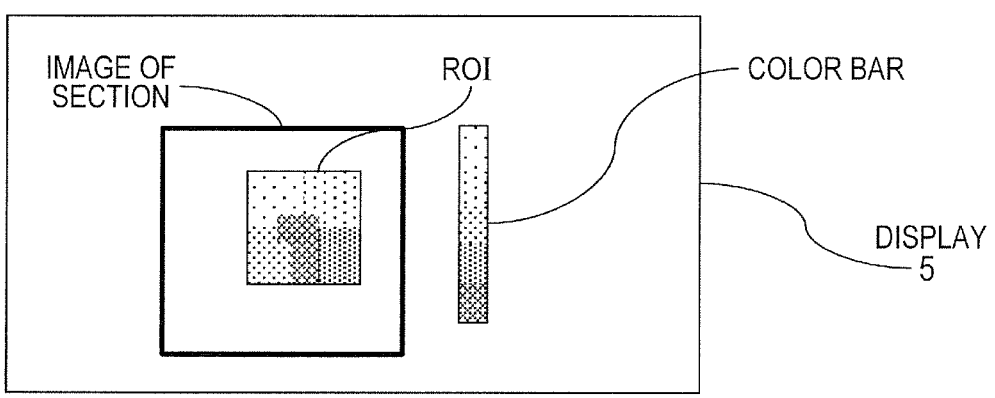

ULTRASOUND DIAGNOSIS APPARATUS

TECHNICAL FIELD

The present invention relates to an ultrasound diagnosis apparatus that detects heterogeneity related to sonic velocity inside a subject by the transmission and reception of ultrasound.

BACKGROUND ART

For a method of diagnosing a mammary tumor, cirrhosis, a lesion of a blood vessel and others, a method (elastography) of diagnosing hardness inside a subject based upon an ultrasonic echo signal in place of palpation by a doctor can be given. In the diagnosis of hardness by elastography, an operator presses a probe on a surface of the subject and generates displacement in a tissue inside a measuring object in a living body and others (hereinafter called a conventional type method). Displacement in a direction of compression is estimated based upon echo signals before and after the compression of the tissue in the living body by pressure, distortion which is a space derivative of the displacement is calculated, and the distortion is imaged. This method has a problem that an imaged object is limited to internal organs that exist in locations in which pressure from a surface of the body is easy. For example, as a slide plane as an intervening layer exists between the surface of the body and the liver, it is difficult to press so that sufficient displacement is generated.

Then, technique for diagnosing hardness by applying radiation pressure to the inside of the subject using an ultrasonic focused beam and displacing a target tissue, inhibiting an effect of the intervening layer can be given. For example, there is acoustic radiation force impulse (ARFI) imaging disclosed in a patent literature 1. In this technique, the displacement of a tissue generated in a direction in which a focused beam advances is imaged and a modulus of elasticity such as a modulus of elasticity in shear and Young's modulus is calculated based upon the estimate of the propagation velocity of a shear wave generated in a direction perpendicular to the direction in which the focused beam advances according to the displacement of the tissue at a focus. When this technique is used, diagnosis in which dependence upon manual technique is reduced is expected because the tissue is displaced by ultrasound in addition to the effect of reducing the effect of the intervening layer such as the slide plane.

When heterogeneity related to sonic velocity exists in the tissue in a measuring range, the measured modulus of elasticity has a value including the propagation velocity of plural shear waves. For a cause of the heterogeneity of sonic velocity, tissue structure, frequency dispersion, an amplitude, particle velocity and others can be given. For example, as for frequency dispersion, a nonpatent literature 1 and a nonpatent literature 2 can be given.

CITATION LIST

Patent Literature

Patent Literature 1: US Patent No. 2004068184

Nonpatent Literature

Nonpatent Literature 1: Deffieux et al., IEEE Trans Medical Imaging, Vol. 28, No. 3, 2009.

Nonpatent Literature 2: Chen et al., IEEE Trans. Ultrason. Ferro. Freq. Contr., Vol. 56, No. 1, 2009.

SUMMARY OF INVENTION

Technical Problem

Heretofore, when the velocity of a shear wave is estimated, the heterogeneity of sonic velocity that proceeds from tissue structure has been not considered. That is, it is supposed that the velocity of the shear wave is the same in a tissue in a measuring range. Accordingly, when tissues having different sonic velocity exist in a measuring visual field, the equalized propagation velocity of the shear wave and a modulus of elasticity are measured. If the heterogeneity of sonic velocity that proceeds from tissue structure is imaged and can be diagnosed, the method can be one of methods of identifying difference between a normal tissue and a malignant tissue.

An object of the present invention is to provide an ultrasound diagnosis apparatus that enables the detection of heterogeneity related to sonic velocity inside a subject by the transmission and reception of ultrasound.

Solution to Problem

To achieve the object, the present invention provides an ultrasound diagnosis apparatus which is provided with an ultrasound probe that received and transmits an echo signal from the inside of a subject, a displacement generating unit that radiates an ultrasonic focused beam onto the subject and displaces a tissue and a displacement detecting unit that receives the echo signal from the subject and detects a temporal waveform of the displacement of a shear wave generated by the ultrasonic focused beam in plural positions and in which the displacement detecting unit is provided with a heterogeneity detecting device that evaluates the heterogeneity of the subject based upon the detected temporal waveform of the displacement of the shear wave.

Besides, to achieve the object, the present invention provides an ultrasound diagnosis apparatus which is based upon the ultrasound diagnosis apparatus that diagnoses a subject by ultrasound, which is provided with an ultrasound probe that receives and transmits an echo signal from the subject, a displacement generating unit that radiates an ultrasonic focused beam onto the subject and displaces a tissue and a displacement detecting unit that receives the echo signal from the subject and detects a temporal waveform of the displacement of a shear wave generated by the ultrasonic focused beam in plural positions and in which the displacement generating unit is provided with a transmission beam generating device for generating displacement that generates the ultrasonic focused beam and a beam frequency setting device that sets a frequency of the ultrasonic focused beam and the displacement detecting unit is provided with a heterogeneity detecting device that evaluates the heterogeneity of the subject based upon the detected displacement of the shear wave.

That is, to achieve the object, in a preferred embodiment of the present invention, a means that detects the heterogeneity of sonic velocity in a tissue radiates focused ultrasound onto the tissue in a living body so as to generate a shear wave, acquires at least two informations from temporal waveforms of the displacement in plural positions of the generated shear wave, measures physical quantity related to the heterogeneity of sonic velocity that proceeds from tissue structure and displaces it.

Advantageous Effects of Invention

According to the present invention, it can be diagnosed whether there is a part heterogeneous in sonic velocity in a measuring object or not by imaging heterogeneity related to sonic velocity that proceeds from tissue structure based upon the waveform of the shear wave generated by the ultrasonic focused beam.

Besides, the imaging and the diagnosis of the heterogeneity of sonic velocity caused by frequency dispersion and an amplitude in addition to heterogeneity related to sonic velocity that proceeds from tissue structure are enabled. Further, the higher-precision evaluation of heterogeneity is enabled by the application of a burst chirp mode.

Furthermore, the application to a diagnostic method of identifying a normal tissue and a malignant tissue based upon a degree of heterogeneity of the present invention is expected.

BRIEF DESCRIPTION OF DRAWINGS

FIG. 3 is an explanatory drawing for explaining the generation of an ultrasonic beam in the first embodiment.

FIG. 9 is an explanatory drawing for explaining an example of screens that display heterogeneity in the first embodiment.

DESCRIPTION OF EMBODIMENTS

Figure 1:
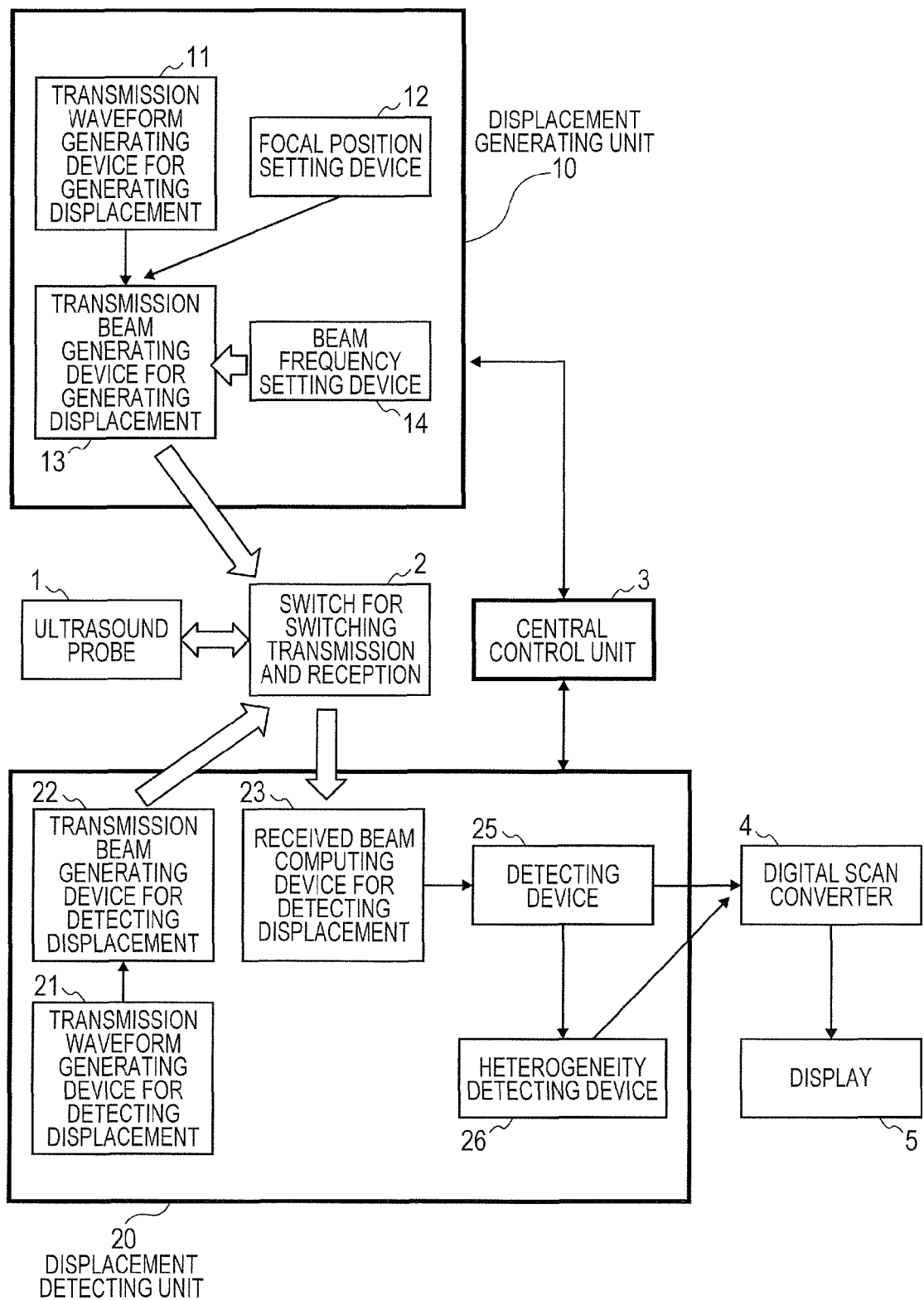
FIG. 1 is a block diagram showing an ultrasound diagnosis apparatus in first to fourth embodiments.

Referring to the drawings, embodiments of the present invention will be described below. FIG. 1 shows the configuration of the whole apparatus according to first to fourth embodiments.

FIG. 1 includes an ultrasound probe 1 that transmits or receives an ultrasonic beam to/from a subject not shown, a displacement generating unit 10 that generates displacement in the subject, a displacement detecting unit 20 that detects the displacement generated in the subject and a central control unit 3 for controlling the displacement generating unit 10 and the displacement detecting unit 20. The ultrasound probe 1 is connected to a transmission beam generating device for generating displacement 13, a transmission beam generating device for detecting displacement 22 and a received beam computing device for detecting displacement 23 via a switch for switching transmission and reception 2 that functions as a part for switching transmission and reception. A beam frequency setting device 14 sets a frequency of a focused ultrasonic beam transmitted from the transmission beam generating device for generating displacement 13. Though the following is not shown in FIG. 1, the central control unit 3 also directly or indirectly controls the switch 2 that functions as the part for switching transmission and reception.

First, the displacement generating unit 10 will be described. The transmission beam generating device for generating displacement 13 is controlled by the central control unit 3 so that the transmission beam generating device applies delay time and weight to a transmission signal every device from the ultrasound probe 1 using a waveform generated in a transmission waveform generating device for generating displacement 11 so as to focus the ultrasonic beam in a position set by the a focused position setting device 12. An electric signal from the transmission beam generating device for generating displacement 13 is converted to an ultrasonic signal in the ultrasound probe 1 and the ultrasonic beam for generating displacement is radiated toward a subject not shown. Radiation start time and radiation termination time of the ultrasonic beam for generating displacement are set in the beam frequency setting device 14. A beam frequency means a repetition frequency in the radiation of the ultrasonic beam for generating displacement.

Next, the displacement detecting unit 20 will be described. After the irradiation of the ultrasonic beam for generating displacement, an ultrasonic beam for detecting displacement for detecting the displacement of a tissue in the subject is radiated. The transmission beam generating device for detecting displacement 22 is controlled by the central control unit 3 so that the transmission beam generating device applies delay time and weight to a transmission signal every device from the ultrasound probe 1 using a waveform generated in a transmission waveform generating device for detecting displacement 21 so as to focus an ultrasonic beam for detecting displacement in a desired position like the ultrasonic beam for generating displacement. An echo signal reflected in the subject and returned to the probe is converted to an electric signal in the ultrasound probe 1 and is transmitted to the received beam computing device for detecting displacement 23. After signal processing such as the detection of an envelope, the compression of a log, a band-pass filter and gain control is applied to the output of the received beam computing device for detecting displacement 23 in a detecting device 25, a value related to heterogeneity is calculated in a heterogeneity detecting device 26. The outputs of the detecting device 25 and the heterogeneity detecting device 26 are converted to a picture signal in a scan converter 4 and the picture signal is displayed as a numeric value and an image respectively showing hardness on a display 5.

The central control unit 3, the heterogeneity detecting device 26 and others which are a part of a block shown in FIG. 1 can be realized by the execution of a program in a central processing unit (CPU) that functions as a processing unit.

First Embodiment

Figure 2:
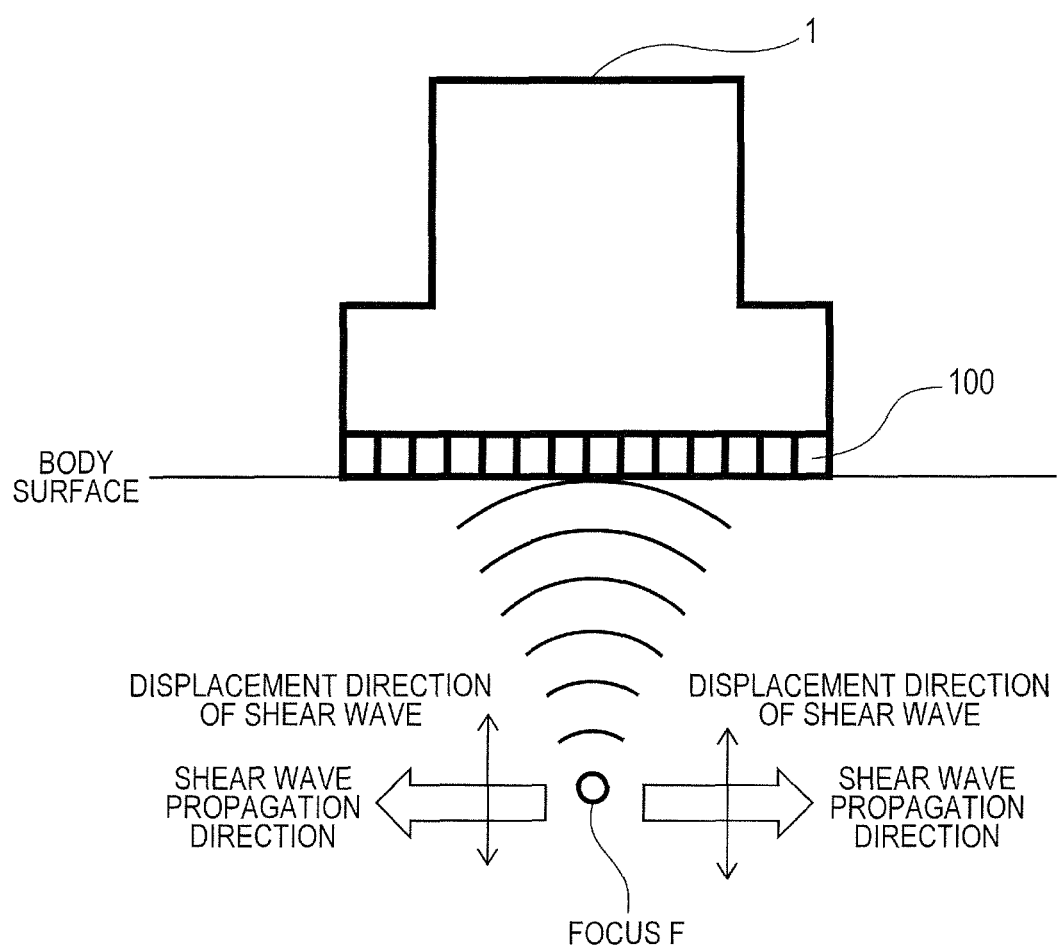
FIG. 2 shows measurement by an ultrasound probe in the first embodiment.

In this embodiment, as shown in FIG. 2, a case that a linear array type ultrasound probe 1 is touched to a surface of a body of a subject and an ultrasonic beam for generating displacement is focused on a target section in the body will be described. In this case, a case that a direction of the propagation of the ultrasonic beam for generating displacement (=the transmission beam for generating displacement) on the desired section is a direction perpendicular to the body surface will be described.

As shown in upper and lower halves of FIG. 3, the generation of an ultrasonic beam is realized by calculating distance between each focus and a position of each element 100 of the ultrasound probe 1, allocating delay time calculated by dividing difference in distance among elements by the sonic velocity of an object every element and transmitting the ultrasonic beam. When an ultrasonic beam for generating displacement is radiated onto a focus, radiation pressure is generated according to the absorption and the scattering of ultrasound by propagation. Normally, the radiation pressure gets maximum in the focus and displacement is generated in a tissue of a living body in an area of the focus. Besides, when the radiation of the ultrasonic beam for generating displacement is stopped, an amount of displacement is lessened. As schematically shown in FIG. 2, a shear wave is generated in a horizontal direction with the surface of the subject with the focus as a starting point by the generation of the radiation pressure.

Figure 4:
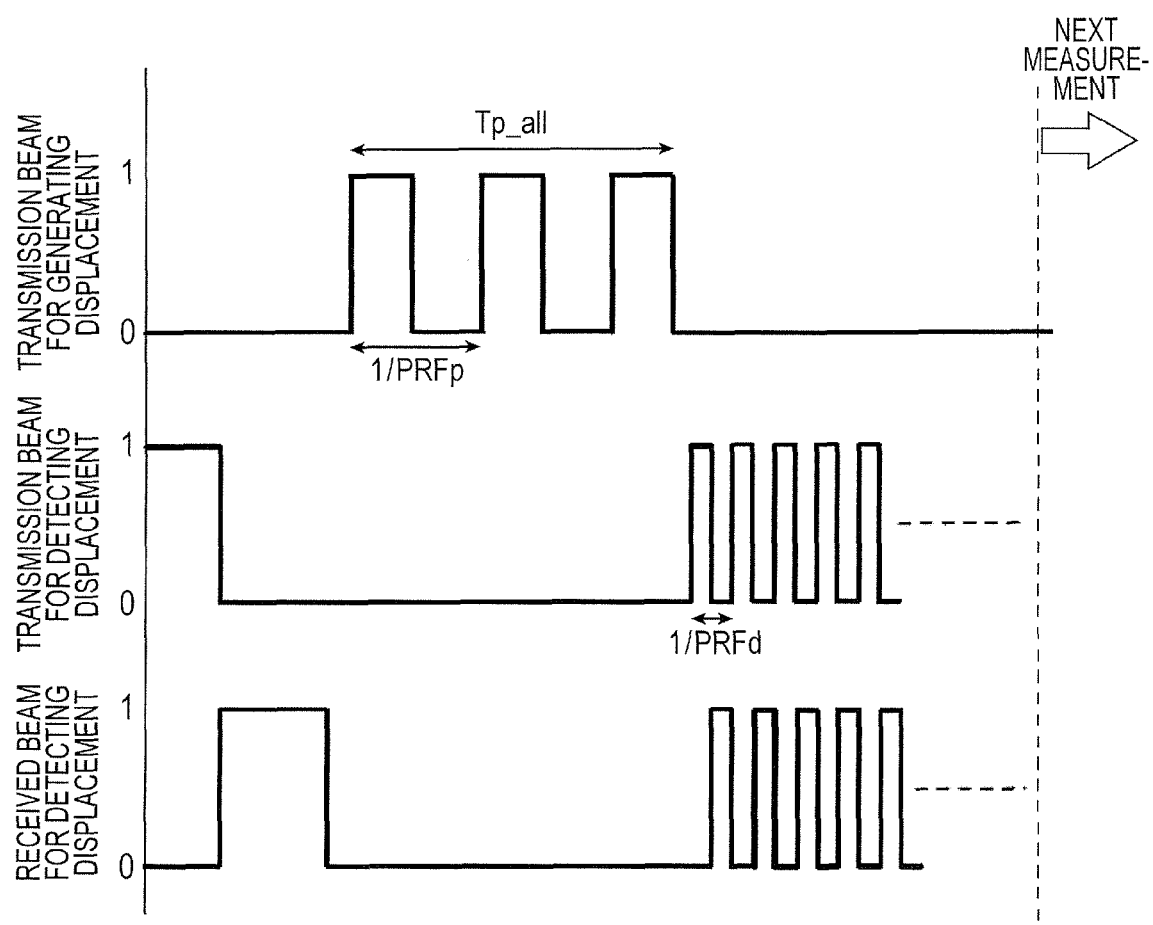
FIG. 4 shows a sequence of the transmission/reception of ultrasonic beams in the first embodiment.

Next, a method of transmitting and receiving an ultrasonic beam by the ultrasound probe 1 will be described using FIG. 4. FIG. 4 shows radiation sequence of a transmission beam for generating displacement, a transmission beam for detecting displacement and a received beam for detecting displacement. The beams are radiated in the order of the transmission beam for detecting displacement and the received beam for detecting displacement and a reference signal used in operation for detecting the displacement of a shear wave is acquired. Turning on/off is controlled based upon an amplitude value of voltage for example, the beam is turned on at the time of 1, and the beam is turned off at the time of 0. Unless hereinafter especially specified, the beam is turned on at the time of 1 and the beam is turned off at the time of 0. When the transmission beam is turned on, it is radiated. Turning on the received beam means that the transmission beam generating device for detecting displacement 22 and the ultrasound probe 1 are disconnected in the switch for switching transmission and reception 2, the received beam computing device for detecting displacement 23 and the ultrasound probe 1 are connected and a phasing add operation for the acquisition of a received signal and the generation of the beam is performed.

First, the transmission beam for detecting displacement and the received beam for detecting displacement are sequentially turned on and a reference signal is acquired from the ultrasound probe 1. After the reference signal is acquired, the transmission beam for generating displacement is radiated onto a focus F and a shear wave is generated. At this time, a frequency of repeatedly transmitted pulses (PRFp) in the radiation of the transmission beam for generating displacement is set in the beam frequency setting device 14 and the beam is radiated at the frequency PRFp plural times. This art has a characteristic that not a frequency of a carrier signal of the transmission beam for generating displacement but the frequency PRFp for turning on/off is controlled and heterogeneity is measured. Imaging at narrow beam width and high spatial resolution is enabled by increasing a frequency of a carrier. In FIG. 4, the transmission beam for generating displacement is radiated three times for example, however, the frequency is not limited to this. As the beam is radiated more times, the bandwidth of PRFp is turned narrow and resolution for the frequency of the transmission beam for generating displacement is enhanced. In the meantime, the beam is often radiated only once and FIGS. 5 and 6 show the temporal variation of displacement using a case that the beam is radiated only once for an example. This is for the following reason. On a normal transmission condition, beam width in an azimuth is approximately 1 mm and when the sonic velocity of a shear wave is 1 m/s and PRFp is 1 kHz, the wavelength is equal to width (beam width in the azimuth) at which radiation pressure for generating the shear wave is generated. That is, to increase displacement, it is desirable that PRFp is 1 kHz or less. However, when PRFp is 1 kHz or less, that is, PRFp is longer than 1 ms, the risk of the rise of temperature increases. As radiation pressure is proportional to the square of pressure and the rise of temperature is proportional to the product of the square of pressure and irradiation time, the ratio of radiation pressure and the rise of temperature is in inverse proportion to irradiation time. Therefore, too long irradiation time is not suitable for making safety and the acquisition of great displacement compatible. When these are considered, it is desirable that a frequency of irradiation is once. To detect the displacement of a shear wave after the irradiation of the beam for generating displacement, the transmission beam for detecting displacement and the received beam for detecting displacement are sequentially turned on.

In the detecting device 25 shown in FIG. 1, normal signal processing such as a band-pass filter is performed and a signal equivalent to PRFp is extracted from a signal acquired by the transmission beam for detecting displacement and the received beam for detecting displacement. The processing by the band-pass filter and others may be also omitted. The displacement of the shear wave is calculated using the reference signal acquired precedently and the signal acquired by the transmission beam and the received beam respectively for detecting displacement after the irradiation of the transmission beam for generating displacement. Correlation operation and the detection of phase difference which are respectively well-known art and others are used for calculating displacement and operation for detecting displacement is performed in the heterogeneity detecting device 26. The transmission beam and the received beam respectively for detecting displacement are repeatedly turned on at a repetition frequency PRFd and the temporal waveform of the displacement (a few μm to a few tens μm) of the shear wave is detected. The PRFd is set so that Nyquist's theorem is met for an estimated frequency of the shear wave. For example, when a raster for detecting displacement is the same as a direction of the displacement of the shear wave, the PRFd is set to the double or more of the frequency of the shear wave.

The PRFd is set in the transmission waveform generating device for detecting displacement 21.

Figure 5A:
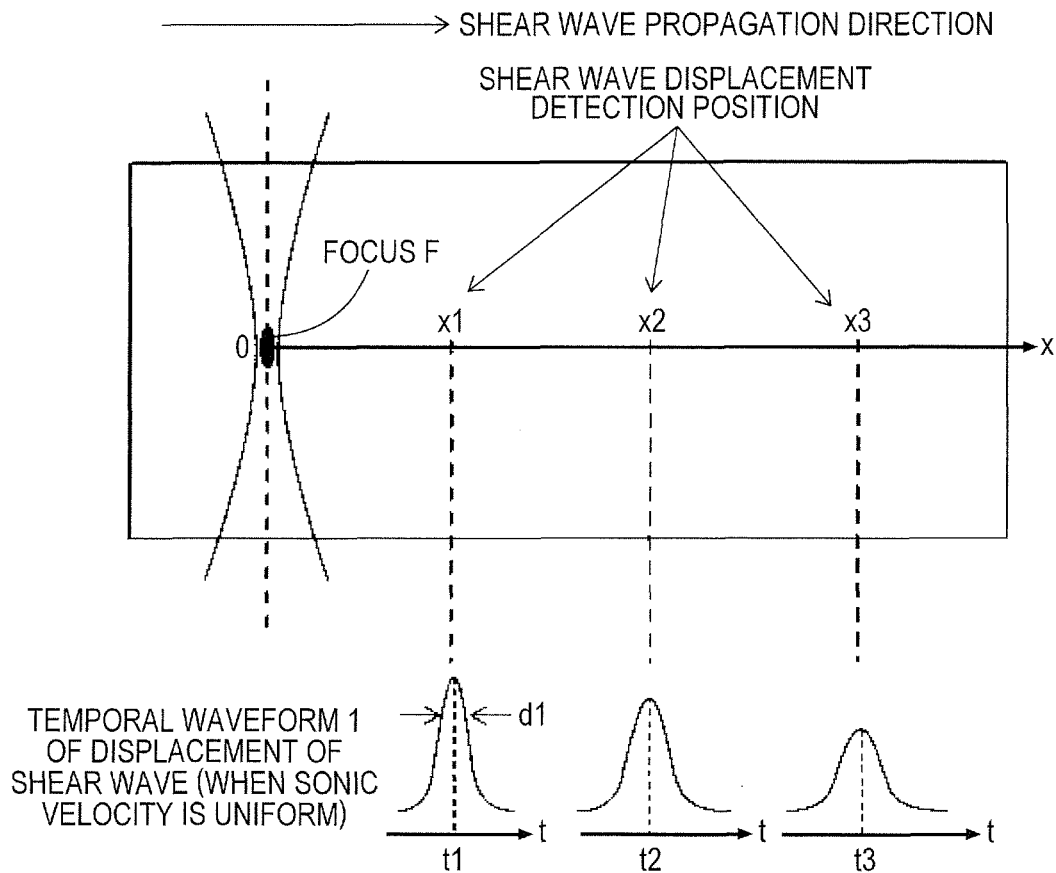
FIG. 5A is an explanatory drawing for explaining the displacement of a shear wave in the case of a tissue the sonic velocity of which is uniform in the first embodiment.
Figure 6:
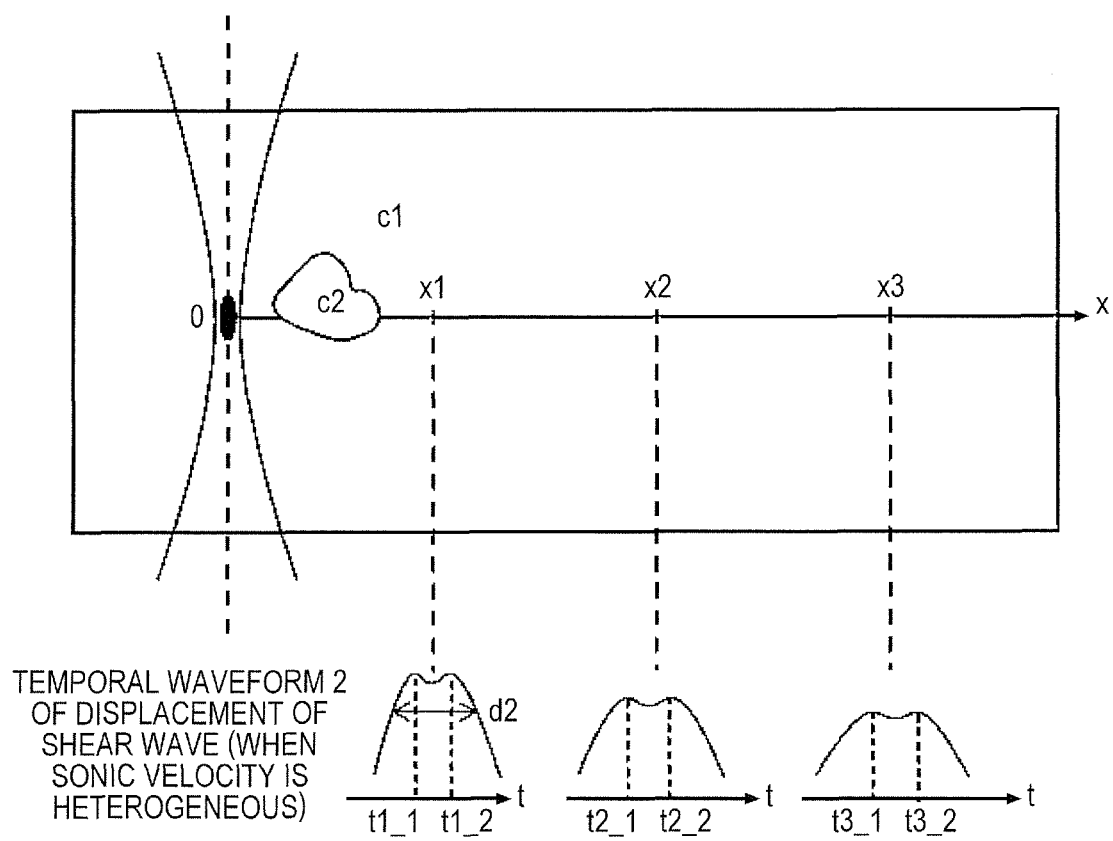
FIG. 6 is an explanatory drawing for explaining a temporal waveform of the displacement of a shear wave in the case of a tissue the sonic velocity of which is heterogeneous in the first embodiment.

FIGS. 5A and 6 show the temporal variation of the displacement of the shear wave (=an amplitude value of the shear wave) in a displacement detection position. The displacement detection position is along a direction of the propagation of the shear wave as shown in FIG. 5A for example and the displacement is detected in plural positions x1, x2, x3 arranged at an equal interval. In this case, a position of a focus is set to "x=0", and x1, x2 and x3 have relation of "x1<x2<x3".

Figure 5B:
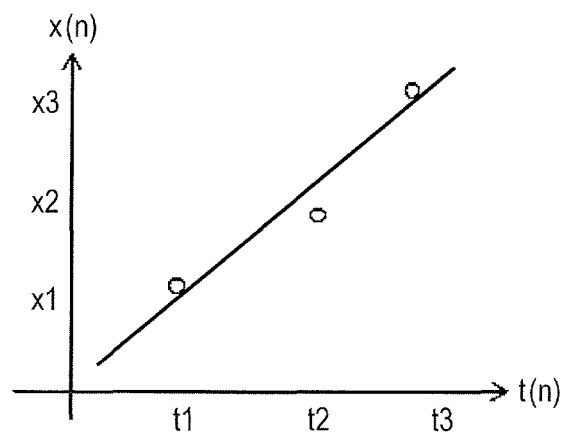
FIG. 5B is an explanatory drawing for explaining a temporal waveform of the displacement of a shear wave in the case of the tissue the sonic velocity of which is uniform in the first embodiment.

First, a case that tissues on a path of the propagation of the shear wave have structure in which sonic velocity that proceeds from tissue structure is uniform will be described referring to FIGS. 5A and 5B (refer to Proceedings of Symposium on Ultrasonic Electronics, Vol. 30, 2009, pp. 525 to 526 by Tabaru and others). In this case, sonic velocity means the propagation velocity of the shear wave. As the shear wave generated at the focus F reaches in the order of the positions x1, x2, x3, being propagated, time t1, t2, t3 at which a temporal waveform of displacement observed in each position x reaches a peak have relation of "t1<t2<t3". As shown in FIG. 5B, the sonic velocity (=the propagation velocity) c of the shear wave is estimated based upon an inclination having a position x (n) as an axis of ordinates and having time t (n) to be a peak as an axis of abscissas in the heterogeneity detecting device 26 described in detail later. However, n is a positive integer and in FIGS. 5A and 5B, n=1, 2, 3. Young's modulus and an elastic modulus such as the elastic modulus of a shear wave are calculated using the estimated propagation velocity of the shear wave. For example, the elastic modulus (=$\rho c^2$) of the shear wave or Poisson's ratio of the shear wave is set to 0.5 based upon the sonic velocity c of the shear wave and tissue density $\rho$ and the elastic modulus such as Young's modulus (=E:3 $\rho c^2$) can be calculated.

Next, a case that two tissues having different sonic velocity exist on a path of the propagation of the shear wave will be described using FIG. 6. In this case, the tissues of the sonic velocity c1, c2 (c1>c2) of the shear wave shall exist in 0<x<x1. At this time, time t1_1 until the shear wave generated at the focus F reaches the displacement detection position x1 and at which the tissue having the sonic velocity c1 is passed is earlier than time t1_2 at which the tissue having the sonic velocity c2 is passed. Accordingly, two peak values emerge in a temporal waveform showing the displacement of the shear wave in the position x1. A temporal waveform also similarly has two peak values in the positions x2, x3.

In this case, the number of the detection positions is 3, however, the number is not limited to 3. An interval Δx of the position x shall be an interval small enough for a wavelength λ of the shear wave, for example, 1/10λ. However, the wavelength is calculated as c/PRFp. It is desirable that a smaller value of supposed minimum velocity in a target part for heterogeneity to be measured or difference in the velocity of the shear wave (Δc=c1−c2) determined by the required resolution of the velocity of the shear wave is used for the sonic velocity c of the shear wave used for calculating the wavelength.

As shown in FIG. 6, as a temporal waveform of the displacement of the shear wave is a waveform in which plural waveforms of the displacement of the shear wave are shifted in a temporal direction and are added in the tissue in which sonic velocity that proceeds from tissue structure is heterogeneous, compared with a case of a tissue in which sonic velocity that proceeds from tissue structure is uniform, the width of a waveform is extended. Accordingly, width d2 in the position x1 shown in FIG. 6 has a larger value than width d1 in the position x1 shown in FIG. 5A. These d1 and d2 are defined as half-width and −6 dB width for example.

In this embodiment, the heterogeneity detecting device 26 shown in FIG. 1 acquires at least two types of information based upon the plural temporal waveforms of the displacement of the shear wave and evaluates the heterogeneity of sonic velocity that proceeds from structure. For a method of evaluating heterogeneity, a degree of a spread in width of the temporal waveforms of the displacement of the shear wave is calculated for example. The width of the temporal waveforms is defined as a value acquired by calculating an integrated value and a maximum amplitude value based the temporal waveforms of the displacement of the shear wave as two information contents and dividing the integrated value by the maximum value for example.

It is desirable for the following reason that at least two types of information, that is, the integrated value and the maximum amplitude value are calculated based upon the plural temporal waveforms in half-width of the displacement of the shear wave and the value acquired by dividing the integrated value by the maximum amplitude value is used for the width of the temporal waveforms. The half-width is a calculating method of searching two points having a half value of a maximum amplitude in the waveforms and setting distance between the two points (time difference between two times because an axis of abscissas shows time in this case) as width. Therefore, in the case of the waveform having the two peaks shown in FIG. 6, four or more points having a half value of the maximum amplitude emerge when an amplitude of a concave portion between the two peaks is lower than a half of the maximum amplitude. When the two peaks are substantially equal, the half-width can be acquired from difference between a half value at the earliest time and a half value at the latest time even if the four or more points having a half value are acquired, however, as the amplitudes of the two peaks are actually not necessarily equal, the half-width becomes half-width of only components in which the velocity of the shear wave is fast or only components in which the velocity of the shear wave is slow according to propagation or becomes half-width of the peaks including both, and therefore, half-width quantitatively acquired may be not the qualitative tracking of the same phenomenon. Besides, in the example of the waveforms shown in FIG. 6, no noise is included, however, when a maximum amplitude is searched in a state including noise, an error is included in an estimate of a value of the maximum amplitude depending upon the magnitude of noise and an error is also included in an estimate of a half value. As a result, in a case that signal-to-noise ratio is not satisfactory, it is not necessarily desirable that beam width is estimated based upon half-width. The half-width has been described for an example, however, the above-mentioned two problems cannot be conquered in principle by operation for searching a location in which fixed displacement can be acquired for maximum displacement on the temporal waveform, for example, by an estimate of the width of the temporal waveform using −20 dB width and −40 dB width.

Then, in this embodiment, a value acquired by dividing an integrated value by a maximum amplitude is used for an index for showing the width of a temporal waveform. First, in the case of an integrated value, even if a temporal waveform has plural peaks, its effect is small. Besides, as operation for integration similarly functions as a low-pass filter that inhibits a high-frequency component, noise hardly has an effect.

As for heterogeneity shown in FIG. 6, effect that sonic velocity is different depending upon a location in a living body and effect described in the following embodiment that frequencies of the sonic velocity of a shear wave are dispersed may be mixed. It is desirable that to generate a shear wave radiated only once and possibly having a single frequency component, an amplitude of the transmission beam for generating displacement has such a shape that a leading edge and a trailing edge are smooth in a hanning waveform. In FIG. 4, the rectangular wave is shown as an example, however, the rectangular wave also includes multiple components of odd times of PRFp such as 3 PRFp and 5 PRFp except PRFp. To inhibit these components, it is well-known that a method of using a hanning waveform is effective.

Next, a processing flow for measuring and evaluating the heterogeneity of sonic velocity that proceeds from structure in the heterogeneity detecting device 26 in this embodiment will be described using a flowchart shown in FIG. 7. As described above, the processing flow in the heterogeneity detecting device 26 can be realized by program processing in CPU. First, diagnosis is started in a step S00. Next, in a step S02, an image of a section is displayed. The displayed image of the section is a B-mode image for example or an image related to hardness such as a distortion rate. In a step S04, a region of interest (ROI) in which heterogeneity is measured is set.

In the measured ROI, the width in a direction of the propagation of a shear wave (in this case, the width in an azimuth) is determined based upon effective propagation distance of the shear wave. Besides, the width (the width in a direction of depth in this case) perpendicular to the direction of the propagation of the shear wave in the measured ROI is determined based upon a direction in which the transmission beam for generating displacement is propagated, for example, the width of a sound source in the direction of the depth in the body in FIG. 2. As the shear wave is propagated, being attenuated, a displacement detection limit value of the ultrasound diagnosis apparatus is exceeded when certain propagation distance is exceeded. Distance to be a displacement detection limit is called effective propagation distance. However, the displacement detection limit value is determined by a parameter such as a dynamic range of the ultrasound diagnosis apparatus and a frequency of the ultrasonic beam for detecting displacement. The effective propagation distance of a shear wave can be determined based upon parameters such as the acoustic intensity of the transmission beam for generating displacement, F-number (=focal distance/an aperture diameter) of the transmission beam for generating displacement, a frequency of the transmission beam for generating displacement, the width of a sound source in a direction in which the transmission beam for generating displacement is propagated, irradiation time of the transmission beam for generating displacement and an amount of maximum displacement of the shear wave.

Figure 8:
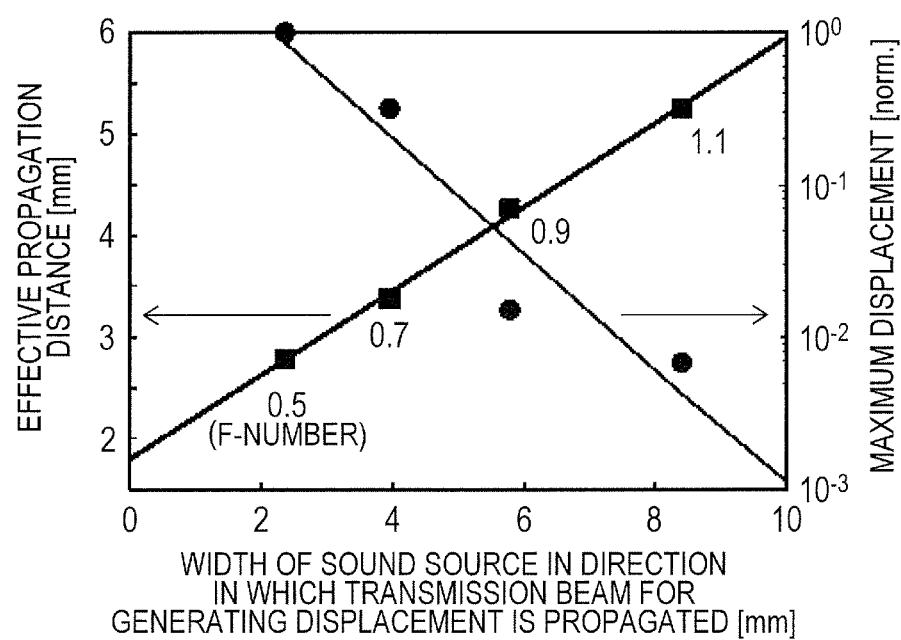
FIG. 8 is an explanatory drawing for explaining parameters for determining the dimension of ROI in the first embodiment.

For example, FIG. 8 shows relation among effective propagation distance, an amount of maximum displacement, F-number and the width of the sound source when a frequency is 2 MHz, irradiation time is 1 ms and instantaneous acoustic intensity is 1 kW/cm$^2$. These parameters are experimentally or calculatively determined beforehand every tissue to be measured and are stored in a storage medium not shown and others. The central control unit 3 determines the size of the optimum ROI based upon a measured part, a radiation parameter of the transmission beam for generating displacement and others in the storage medium.

Otherwise a propagation direction of a shear wave in the ROI has a smaller value than a value experimentally or calculatively determined beforehand, for example 30λ (λ: wavelength of the shear wave).

An operator may also determine a position of the ROI via an input device such as a keyboard, a track ball and a mouse not shown, watching the image of the section displayed on the display 5 in the step S02 or the central control unit 3 may read a position according to a measured part such as a liver and a mammary gland from a storage (a memory) not shown and others and may also determine it. When the operator manually sets, the operator can set the ROI, avoiding a blood vessel and others. Next, in a step S06, the displacement of the shear wave is measured and next in a step S08, the heterogeneity of sonic velocity that proceeds from structure is calculated. In a step S10, a value showing the measured heterogeneity, for example, the width of the temporal waveform is displayed on a screen of the display 5 together with the image of the section. The image of the section is the same as the image of the section displayed in the step S02 or an image of a section imaged at time immediately before or immediately after the evaluation of heterogeneity.

FIG. 9 shows an example of display on the display 5 showing heterogeneity, that is, the width of a temporal waveform. A value of heterogeneity (=the width of the temporal waveform) is displayed in a position close to the ORI for example or on the side of an image of a section on the screen of the display 5 as shown in the uppermost figure in FIG. 9. The width of the temporal waveform is displayed as a mean value of the width of the temporal waveform calculated in each position x (n) in the ROI for example. At this time, standard deviation and others are displayed together with the mean value of the width of the temporal waveform and may be also used for an index for an operator to verify measurement precision.

In another display method, the width of the temporal waveform is displayed in color in the ROI. At that time, as shown in a middle figure in FIG. 9, a color bar corresponding to the width of the temporal waveform is displayed on the same screen and the operator can visually judge a degree of heterogeneity in a measured part. In the color bar, a scaled value according to a measured part is read from the storage not shown and others via the central control unit 3 beforehand and the color bar is scaled. Besides, a space derivative related to the propagation x of a shear wave for the width D of the temporal waveform in each position x (n), that is, dD/dx is calculated and the information of the spatial width of the temporal waveform can be also mapped in the ROI. On the screen at that time, a color map showing the space derivative of the width of the temporal waveform in the ROI and a color bar corresponding to the space derivative of the width of the temporal waveform are displayed as shown in the lowermost figure in FIG. 9 for example. Heterogeneity having higher spatial resolution can be diagnosed by displaying a value of the space derivative.

Figure 7:
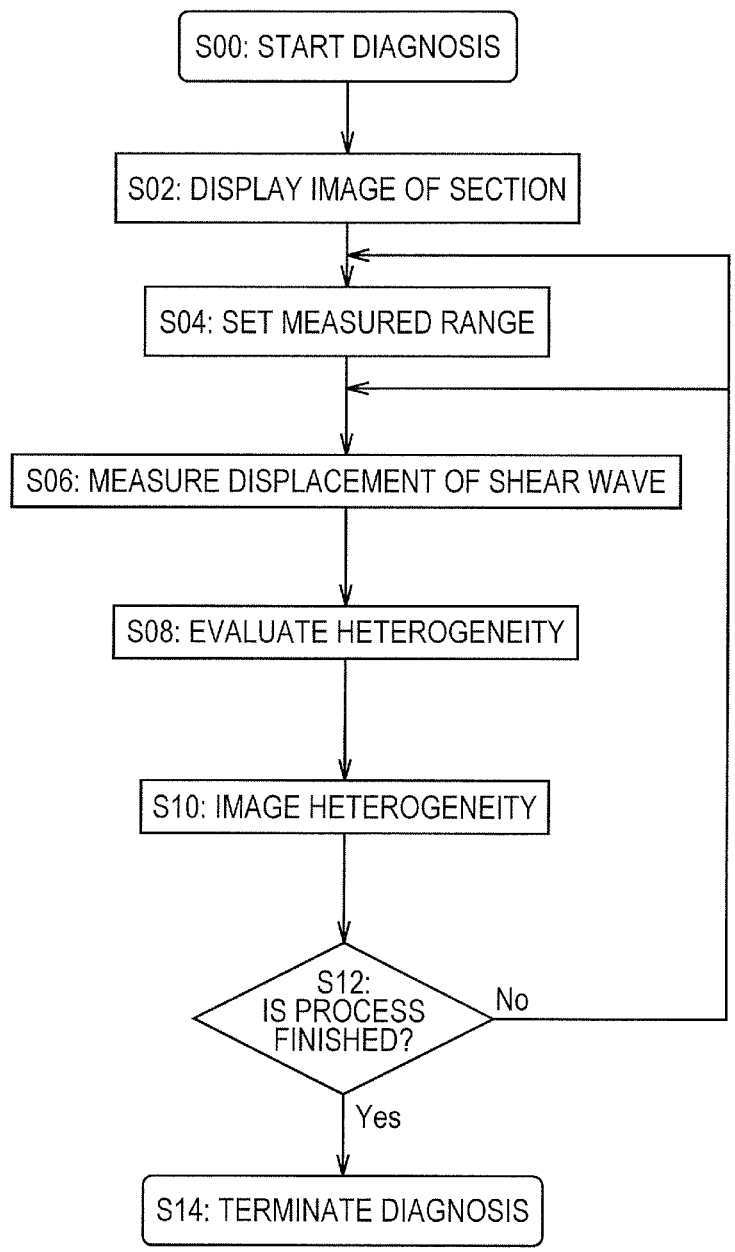
FIG. 7 is a flowchart showing the measurement of heterogeneity in the first embodiment.

When a termination signal is input via the input device not shown in a step S12 shown in FIG. 7, the measurement of heterogeneity is finished in a step S14. Besides, when measurement in the ROI set in the step S04 is required again or when the ROI is set in another position for measurement, control is returned to the step S04 and the step S06 and heterogeneity is continuously evaluated. In the case of measurement in two or more positions, scaling in the color bar may be also varied according to measured plural values of heterogeneity. In the case of measurement in the same ROI, as to the width of the temporal waveform displaced in the uppermost figure in FIG. 9 for example in the step S10, a result every measurement and a mean value of each measurement are included. Besides, when ROI is set in plural positions, ROIs are numbered like ROI1, ROI2 in the uppermost figure in FIG. 9 and the positional information of the ROIs and acquired results of the width of the temporal waveform may be also correlated in the image of the section. In the examples shown in the middle figure and the lowermost figure in FIG. 9, plural ROIs and results of the width of the temporal waveform are displayed in the image of the section.

When measurement is made plural times, imaged parts are differentiated in the preceding and following measurements of heterogeneity because of a motion of the probe and a motion of the body of the subject and accordingly, the positional information of the ROI may be also spatially shifted. When measurement is made plural times, the positional information of the ROI can be also corrected at any time by using Motion Correction (H. Yoshikawa, et. al., Japanese Journal of Applied Physics, Vol. 45, No. 5B, p. 4754, 2006 for example.

In the above-mentioned method of measuring the heterogeneity of the width of the temporal waveform, a direction of the propagation of the ultrasonic beam for generating displacement may be also a diagonal direction in addition to a direction perpendicular to the surface of the body. However, the transmission beam generating device for detecting displacement 22 is controlled so that a direction of a received beam input to the received beam computing device for detecting displacement 23 and a direction in which the shear wave advances are not parallel and both are possibly perpendicular. As a direction of the propagation of the shear wave is a direction of displacement, that is, the direction is perpendicular to a direction of the transmission beam for generating displacement, detection sensitivity for displacement is lost when the direction of the propagation of the received beam and the direction of the propagation of the shear wave are parallel. Therefore, the direction of the propagation of the ultrasonic beam for generating displacement is set so that the direction is desirably perpendicular to the surface of the body.

In the step S04 shown in FIG. 7, an operator may also set the size of the ROI to a desired dimension via an input device not shown in place of setting the size of the ROI to size determined based upon effective propagation distance and the width of a sound source. At this time, when the desired dimension is larger than the optimum size of the ROI, the steps S06 and S08 may be also executed in each position, shifting an optimum position of the ROI.

Second Embodiment

A second embodiment for evaluating heterogeneity based upon plural temporal waveforms of the displacement of a shear wave in a heterogeneity detecting device 26 will be described referring to FIGS. 10A and 10B below.

Figure 10A:
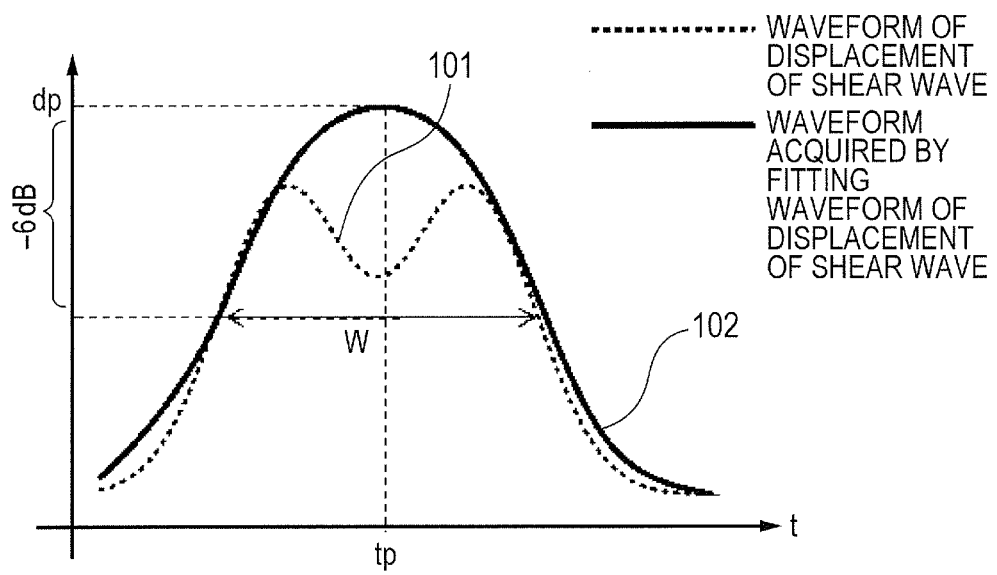
FIG. 10A is an explanatory drawing for explaining one example of a method of calculating heterogeneity in the second embodiment.

As shown in FIG. 10A, in one method, after a temporal waveform 101 of the displacement of a shear wave is fitted using an arbitrary well-known function, for example, a polynomial function, an exponential function, Gaussian function and others, noise is removed using a low-pass filter and others. Afterward, half-width W having a smaller value than a peak value dp of a fitted waveform 102 by −6 dB as a threshold is calculated. Noise removing processing may be also performed before fitting and noise removing processing may be also omitted. After fitting or after noise is removed, the width of the temporal waveform described in the first embodiment may be also calculated. A value related to heterogeneity may be also calculated based upon a function having time tp until the waveform of displacement after fitting reaches a peak, a peak value dp of displacement and a center position (time) of the waveform of displacement in addition to the half-width as a parameter. In this embodiment, for two types of information acquired based upon the temporal waveform of the displacement of the shear wave to evaluate heterogeneity, a peak value and half-width W are used for example.

Figure 10B:
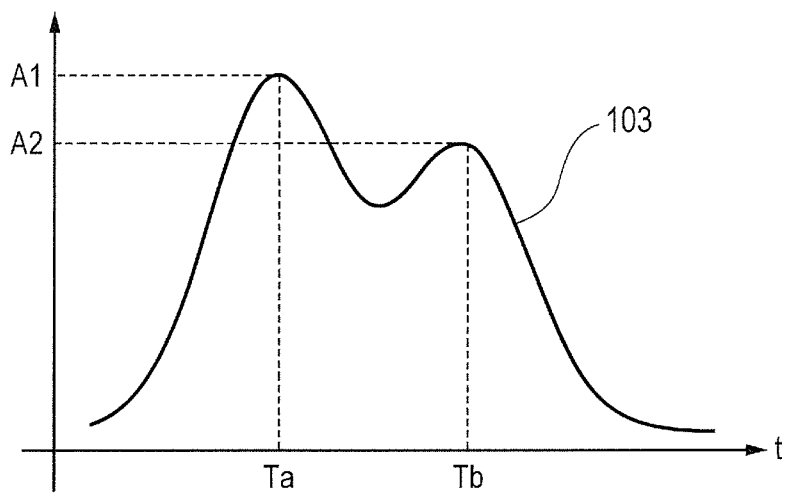
FIG. 10B is an explanatory drawing for explaining another example of a method of calculating heterogeneity in the second embodiment.

Besides, for another method, as shown in FIG. 10B, the following mathematical expression 1 is fitted to a temporal waveform 103 of the displacement of a shear wave.

$$y = A1 * \exp(-(t-Ta)^2/\text{alpha}1) + A2 * \exp(-(t-Tb)^2/\text{alpha}2) \quad (1)$$

At this time, an evaluated value is A1, A2, Ta, Tb, alpha1, alpha2 which are respectively parameters in the mathematical expression 1 or a result of operation using two or more parameters. For example, "Ta−Tb" and "Ta−Tb/((A1+A2)/2)" for two types of information acquired based upon the temporal waveform 103 of the displacement of the shear wave are an evaluated value of heterogeneity. After fitting in the mathematical expression 1, fitting is further performed using the arbitrary well-known function (the polynomial function, the exponential function, the Gaussian function and others) and half-width W may be also calculated.

Corresponding time Ta (n) and Tb (n) in each position x (n) are calculated using the mathematical expression 1, the sonic velocity c1 of the shear wave can be also estimated based upon relation between x (n) and Ta (n), and the sonic velocity c2 of the shear wave can be also estimated based upon relation between x (n) and Tb (n). The method described using FIG. 5B for example can be used for the estimate of the velocity of the shear wave. As described above, when sonic velocity that proceeds from tissue structure is heterogeneous, it is fitted using the mathematical expression 1 and others and if the time of two peak values can be calculated, the existence of media different in velocity can be quantified. For a method of displaying heterogeneity, the sonic velocity c1, c2 of two shear waves can be also displayed and difference between c1 and c2 can be also displayed.

When a location having three or more different sonic velocity exists in the ROI, peak values of the temporal waveform of the shear wave are also 3 or more. A function in the mathematical expression 1 is set according to the number of peaks.

Besides, for another method of evaluating heterogeneity, a value representing heterogeneity may be also the number of peaks in the temporal waveform of the displacement of the shear wave. In the example shown in FIG. 6, the number is 2. The number of peaks is calculated based upon a waveform after fitting or after noise is removed.

Third Embodiment

In a third embodiment, a method of evaluating the heterogeneity of sonic velocity that proceeds from frequency dispersion will be described using FIGS. 11 and 12.

For a cause of the heterogeneity of sonic velocity, tissue structure, frequency dispersion, an amplitude and particle velocity can be given. In the first embodiment, the method of evaluating the heterogeneity of sonic velocity that proceeds from tissue structure is described. When there is the heterogeneity of sonic velocity that proceeds from frequency dispersion and when a repetition frequency PRFp in the radiation of a transmission beam for generating displacement has bandwidth, the velocity of a shear wave varies. In this embodiment, the heterogeneity of sonic velocity that proceeds from frequency dispersion will be mainly described.

Figure 11:
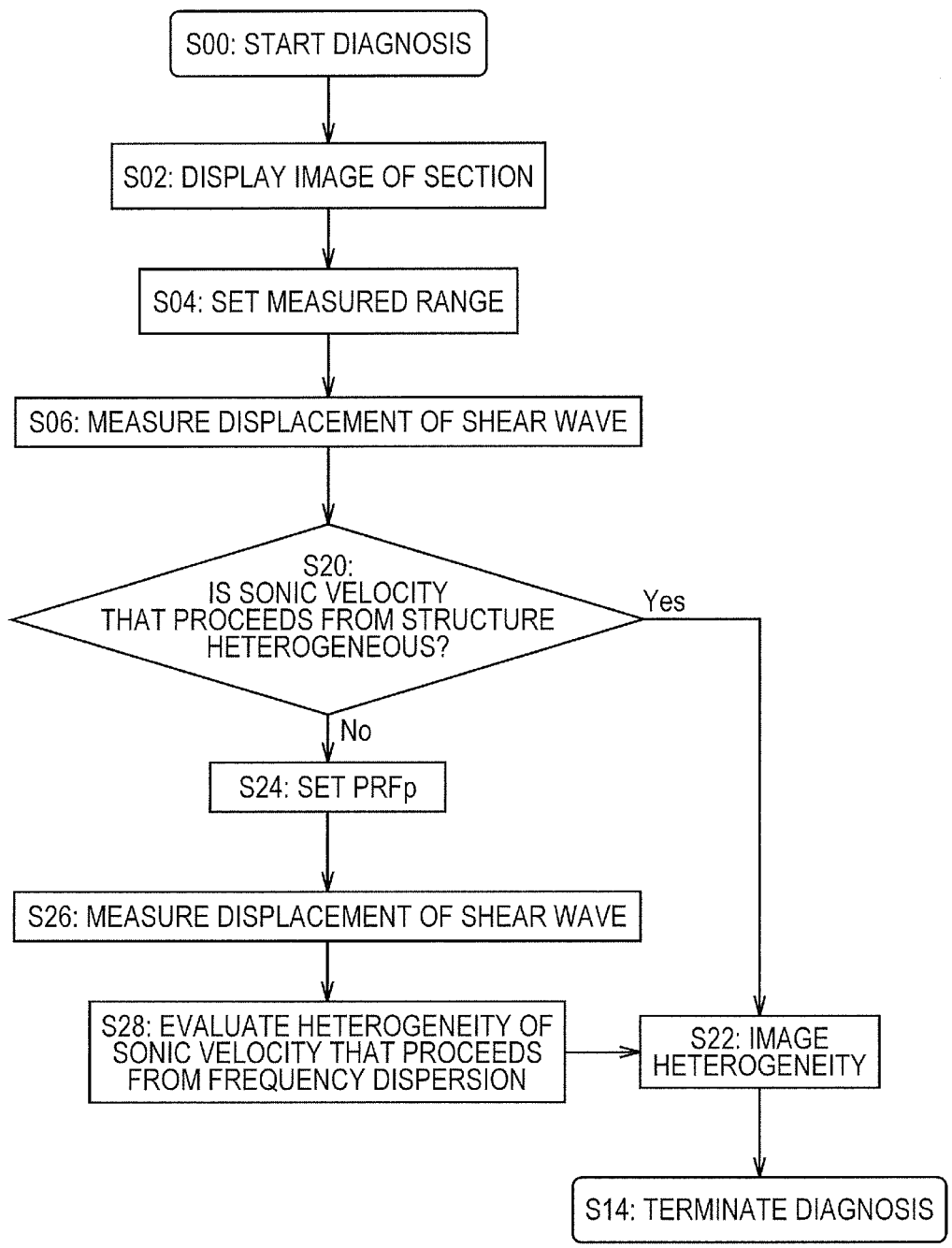
FIG. 11 is a flowchart showing the measurement of heterogeneity in the third embodiment.

FIG. 11 shows a processing flow of the third embodiment in which the heterogeneity of sonic velocity that proceeds from frequency dispersion is measured and evaluated when no heterogeneity of sonic velocity that proceeds from tissue structure exists. As a processing flow of steps S00, S02, S04, S06 is similar to the processing flow in the first embodiment shown in FIG. 7, the description is omitted. In the third embodiment, to simplify description, only a case that heterogeneity is measured in only one ROI will be described, however, as in the first embodiment, heterogeneity may be also measured in different ROIs.

In a step S20, it is judged whether the heterogeneity of sonic velocity that proceeds from tissue structure exists in ROI or not. For a method of judging, for example, standard deviation related to the width of a temporal waveform in ROI and a space derivative (dD/dx) of the width of the temporal waveform, difference between a maximum value and a minimum value and a mean value are compared with a threshold determined every measured part beforehand. The judgment can be executed by a program that realizes a heterogeneity detecting device 26. The threshold is stored in a memory not shown every measured part, may be also read by a central control unit 3, and an operator may also input the threshold via an input device not shown.

When it is judged that the heterogeneity of sonic velocity that proceeds from tissue structure exists, the heterogeneity of the velocity is displayed on a display 5 by the similar method to the method in the first embodiment in a step S22.

When it is judged that no heterogeneity of sonic velocity that proceeds from tissue structure exists, PRFp (m) (m=1, 2, 3, - - - ) is set in a step S24 so as to measure the heterogeneity of sonic velocity that proceeds from frequency dispersion. To measure the heterogeneity of sonic velocity that proceeds from frequency dispersion, the transmission beam for generating displacement is radiated at at least two types of PRFp and the displacement of a shear wave is required to be measured. Accordingly, when the PRFp set in the step S24 is set to a different value from PRFp used for measuring the displacement of the shear wave in the step S06, n is 1 or a larger arbitrary integer. Besides, when the PRFp set in the step S24 includes the PRFp used for measuring the displacement of the shear wave in the step S06, n is 2 or a larger arbitrary integer.

Figure 12:
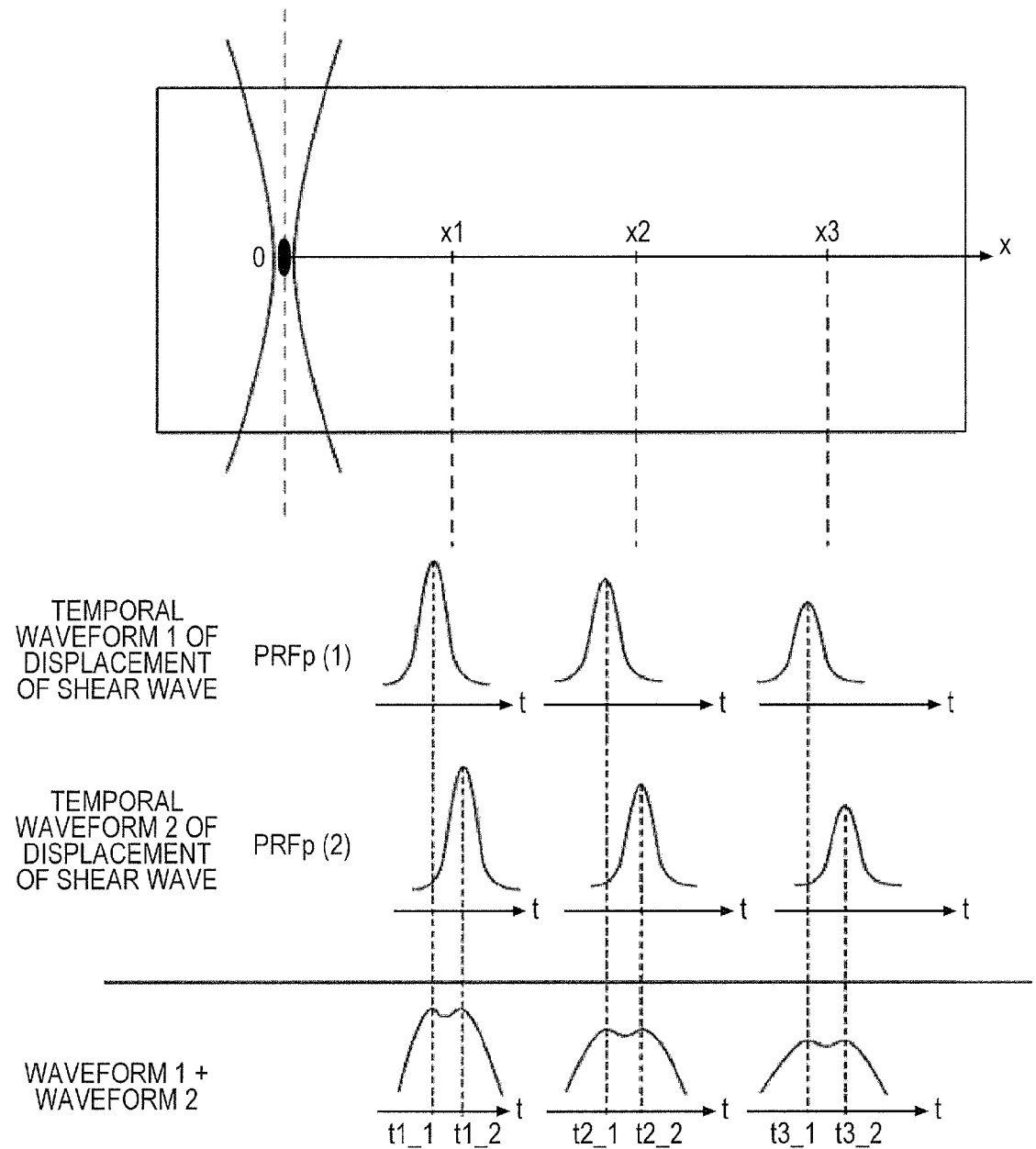
FIG. 12 is an explanatory drawing for explaining a temporal waveform of the displacement of a shear wave in the case of a tissue the sonic velocity of which is heterogeneous in the third embodiment.

When the heterogeneity of sonic velocity that proceeds from frequency dispersion exists, the transmission beam for generating displacement is transmitted at two types of PRFp for example and when the displacement of a shear wave is measured in a shear wave detection position x (n), a temporal waveform shown in FIG. 12 is acquired. When a case that the transmission beam for generating displacement is transmitted at PRFp (1) and a case that the transmission beam is transmitted at PRFp (2) as in the temporal waveform of the displacement of the shear wave shown in FIG. 12 are compared, time at which the displacement of the shear wave reaches a peak varies. This reason is that when the PRFp varies, the velocity of the shear wave propagated in the same medium varies. Accordingly, peak values emerge plural times in a waveform acquired by adding a waveform 1 and a waveform 2.

In the evaluation executed in a step S28 in FIG. 11 of the heterogeneity of sonic velocity that proceeds from frequency dispersion, the similar method to a method of evaluating the heterogeneity of sonic velocity that proceeds from structure is applied. A result of the evaluation of the heterogeneity is imaged in the step S22. For a method of imaging, the similar method to the method in the step S10 in the first embodiment is applied for example.

When the heterogeneity of sonic velocity that proceeds from frequency dispersion is measured, it is desirable that PRFp (m) set by a beam frequency setting device 14 is 40 Hz to a few kHz. Besides, an interval $\Delta PRFp$ (m)(PRFp (m+1)−PRFp (m)) of PRFp (m) is set to an equal interval or according to an arbitrary function. It is desirable that the interval is a few hundred Hz.

The evaluation of the heterogeneity of sonic velocity that proceeds from frequency dispersion can be also tried without evaluating the heterogeneity of sonic velocity that proceeds from structure. In this case, the steps S06, S20 shown in FIG. 11 can be omitted.

The heterogeneity of sonic velocity that proceeds from frequency dispersion can be also applied to the evaluation of the heterogeneity of sonic velocity that proceeds from the displacement (an amplitude) of a shear wave. As the ultrasonic intensity of the transmission beam for generating displacement and the displacement (an amplitude) of a generated shear wave have nonlinear relation, the displacement (the amplitude) of the shear wave may cause the heterogeneity of sonic velocity. The heterogeneity of sonic velocity that proceeds from the amplitude can be evaluated by varying the ultrasonic intensity of the transmission beam for generating displacement when the ultrasonic intensity of the transmission beam for generating displacement is varied in place of varying PRFp (m).

In this embodiment, after the evaluation of the heterogeneity of sonic velocity that proceeds from tissue structure, the heterogeneity of sonic velocity that proceeds from frequency dispersion is evaluated, however, conversely, after the heterogeneity of sonic velocity that proceeds from frequency dispersion is evaluated, the heterogeneity of sonic velocity that proceeds from tissue structure may be also evaluated. Further, the evaluation of heterogeneity may be also made in the arbitrary order of measurement in required items of frequency dispersion, tissue structure and the amplitude.

Besides, when the transmission beam for generating displacement for evaluating the heterogeneity of sonic velocity that proceeds from frequency dispersion is radiated, the transmission beam for generating displacement having a broadband frequency characteristic, that is, like a pulse wave including plural PRFps is radiated only once in place of radiation at a repetition frequency PRFp in the radiation of two or more types of transmission beams for generating displacement, and parameters (the width of a temporal waveform, the velocity of a shear wave and others) related to the heterogeneity may be also calculated. For the transmission beam for generating displacement like a pulse wave, a coded/decoded transmission beam for generating displacement can be used for example. Hereby, as the transmission beam for generating displacement has only to be radiated only once and a shear wave has only to be detected only once, diagnostic time can be reduced. Especially, as described in the first embodiment, the evaluation of the heterogeneity of sonic velocity that proceeds from tissue structure and the evaluation of the heterogeneity of sonic velocity that proceeds from frequency dispersion can be independently performed by controlling a leading edge and a trailing edge in an amplitude of the transmission beam for generating displacement and comparing a case that PRFp is main like a hanning waveform and a case that components of odd times of PRFp such as 3PRFp and 5PRFp are also included except PRFp like a rectangular wave.

Fourth Embodiment

Another method of the method of evaluating the heterogeneity of sonic velocity that proceeds from frequency dispersion in the step S28 in the third embodiment will be described in a fourth embodiment below. The sonic velocity c (m) of a shear wave is estimated based upon a temporal waveform of the displacement of the shear wave acquired in a detection position x for PRFp (m).

Figure 13:
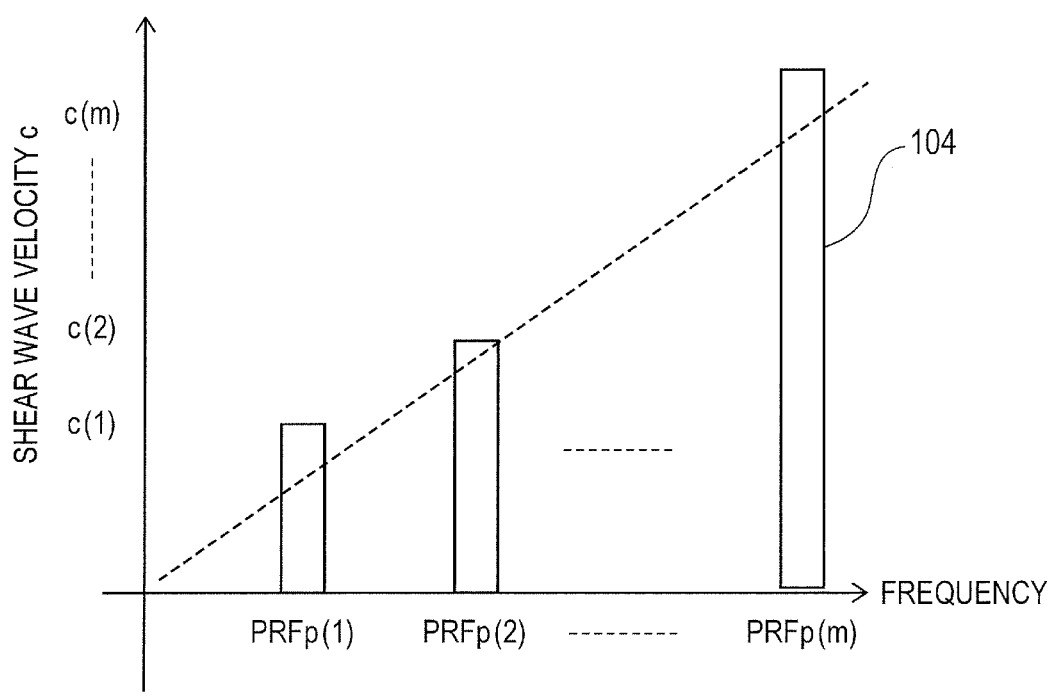
FIG. 13 shows relation between the velocity of a shear wave and a frequency in the fourth embodiment.

FIG. 13 shows a graph 104 showing relation between the sonic velocity c (m) of a shear wave and a repetition frequency PRFp (m) in the radiation of a transmission beam for generating displacement. The heterogeneity of sonic velocity that proceeds from frequency dispersion is calculated as difference dc (=c (m)−c (1) or c (m)−c (m−1)) in the sonic velocity of a shear wave for example. Otherwise the heterogeneity of sonic velocity has a value acquired by multiplying dc by a central position (time) of a waveform of the displacement of a shear wave. Otherwise the heterogeneity of sonic velocity has a value acquired by multiplying dc by time tp at which a waveform of the displacement of a shear wave reaches a peak. The central position (time) and the time tp at which the waveform of the displacement reaches a peak are calculated based upon the waveform of the displacement of the shear wave, a waveform acquired by fitting the waveform of the displacement of the shear wave and a waveform acquired by removing noise after the waveform of the displacement of the shear wave is fitted. It need scarcely be said that the detection of the heterogeneity of sonic velocity in this embodiment can be realized by a program in the heterogeneity detecting device 26 shown in FIG. 1 as in the above-mentioned embodiment.

In this embodiment, the measurement of the heterogeneity of sonic velocity that proceeds from frequency dispersion and at the same time, a frequency of the velocity of a shear wave, that is, dependency upon a repetition frequency in the radiation of the transmission beam for generating displacement and the velocity of a mean shear wave for the frequency can be simultaneously measured.

Fifth Embodiment

Next, an ultrasound diagnosis apparatus that detects the heterogeneity of sonic velocity that proceeds from structure using a burst chirp mode will be described as a fifth embodiment.

Figure 14:
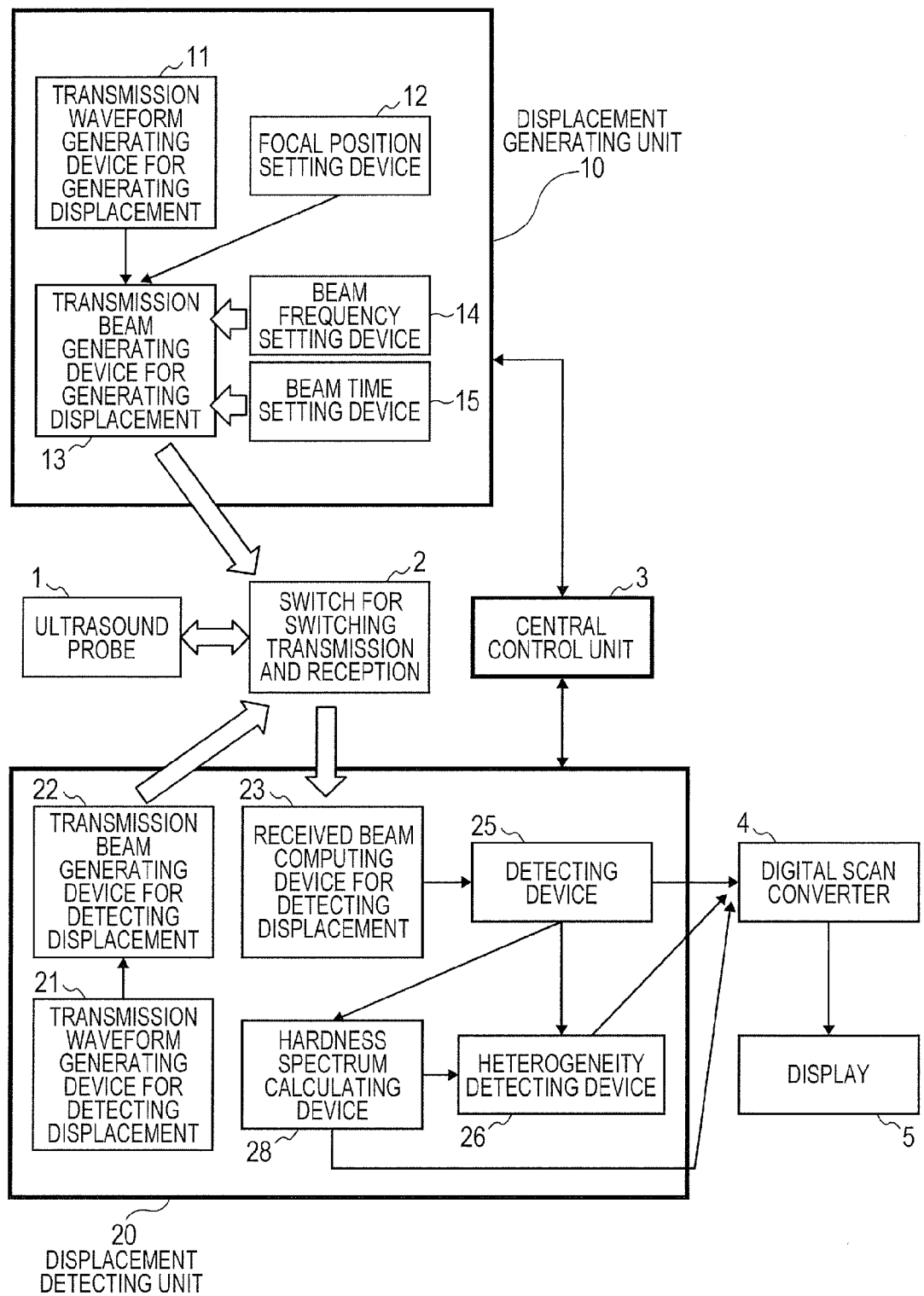
FIG. 14 is a block diagram showing an ultrasound diagnosis apparatus in a fifth embodiment.

FIG. 14 is a block diagram showing a system for executing this embodiment. The system is different from the system described in the first to fourth embodiments in that a beam time setting device 15 is added to a displacement generating unit 10 and a hardness spectrum calculating device 28 is added to a displacement detecting unit 20. The beam time setting device 15 sets the irradiation time of a transmission beam for generating displacement generated by a transmission beam generating device 13 for generating displacement. In the displacement detecting unit 20, after signal processing such as the detection of an envelope, the compression of a log, a band-pass filter and gain control is applied to the output of a received beam computing device for detecting displacement 23 in a detecting device 25, spectrum information of the displacement of a shear wave is calculated in the hardness spectrum calculating device 28. The spectrum information of the displacement of the shear wave calculated in the hardness spectrum calculating device 28 is input to a heterogeneity detecting device 26 and in the heterogeneity detecting device 26, a value related to the heterogeneity is calculated.

Next, a method of transmitting the transmission beam for generating displacement by the burst chirp mode will be described using FIG. 15. At a focus F1 and a focus F2 respectively of a tissue of a subject shown in FIG. 15, two transmission beams for generating displacement are controlled so as to alternately generate displacement. Turning on/off the radiation onto each focus of the transmission beams for generating displacement is controlled in a central control unit 3 and time for switching turning on/off is set in the beam time setting device 16.

Figure 16:
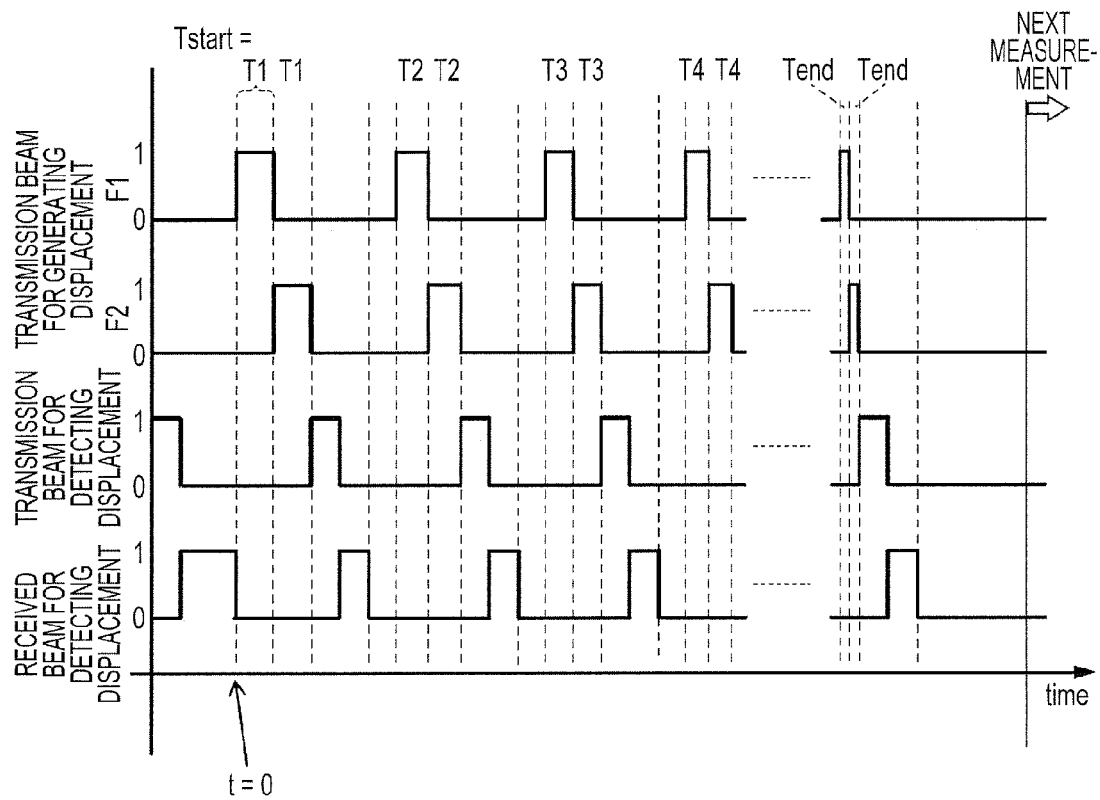
FIG. 16 shows a sequence of a process by the ultrasound diagnosis apparatus in the fifth embodiment.

FIG. 16 shows a sequence of the transmission beam for generating displacement by the transmission beam generating device for generating displacement 13 and transmission/received beams for detecting displacement by a transmission beam generating device for detecting displacement 22 and the received beam computing device for detecting displacement 23. In this case, a mode in which a value of Tm is swept from a large value to a small value is called a burst chirp mode. That is, FIG. 16 shows a sequence of the transmission beam for generating displacement when an interval ΔTm (=T (m+1)−Tm) between switching cycles Tm and T (m+1) is a negative constant. In this case, time at which the first transmission beam for generating displacement is radiated shall be zero.

First, the transmission beam for generating displacement to the focus F1 is turned on (=1) in a state in which the transmission beam for generating displacement to the focus F2 is turned off (=0), displacement is caused at the focus F1, and a shear wave is propagated. The transmission beam for generating displacement to the focus F1 is ordinarily in an ON state at the time of "0≤t≤T1". Next, when time t is T1, the transmission beam for generating displacement to the focus F1 is turned off. At this time, the transmission beam for generating displacement to the focus F2 is turned on, displacement is caused at the focus F2, and a shear wave is propagated. The transmission beam for generating displacement to the focus F1 is turned off and the transmission beam for generating displacement to the focus F2 is turned on at the time of "T1≤t≤T1+T1". In the above-mentioned sequence, the switching cycle of the two transmission beams for generating displacement is T1.

When the radiation of the transmission beam for generating displacement by the burst chirp mode is finished, the transmission beam for detecting displacement and the received beam are next sequentially turned on.

Next, the switching cycle Tm for turning on/off the transmission beam for generating displacement is changed, and the radiation of the transmission beam for generating displacement and the detection of displacement are performed. In this case, "m" represents a cycle in which the focus F1 and the focus F2 are turned on at the "m"th time and m is 1, 2, 3, - - - . The magnitude of the acoustic intensity a burst onto each focus may be also the same or may be also different. Shear waves generated at the focus F1 and at the focus F2 interfere with each other, being propagated according to the irradiation of the transmission beam for generating displacement, negate each other, and amplify each other. In the meantime, heat is caused at each focus together with displacement.

Figure 15:
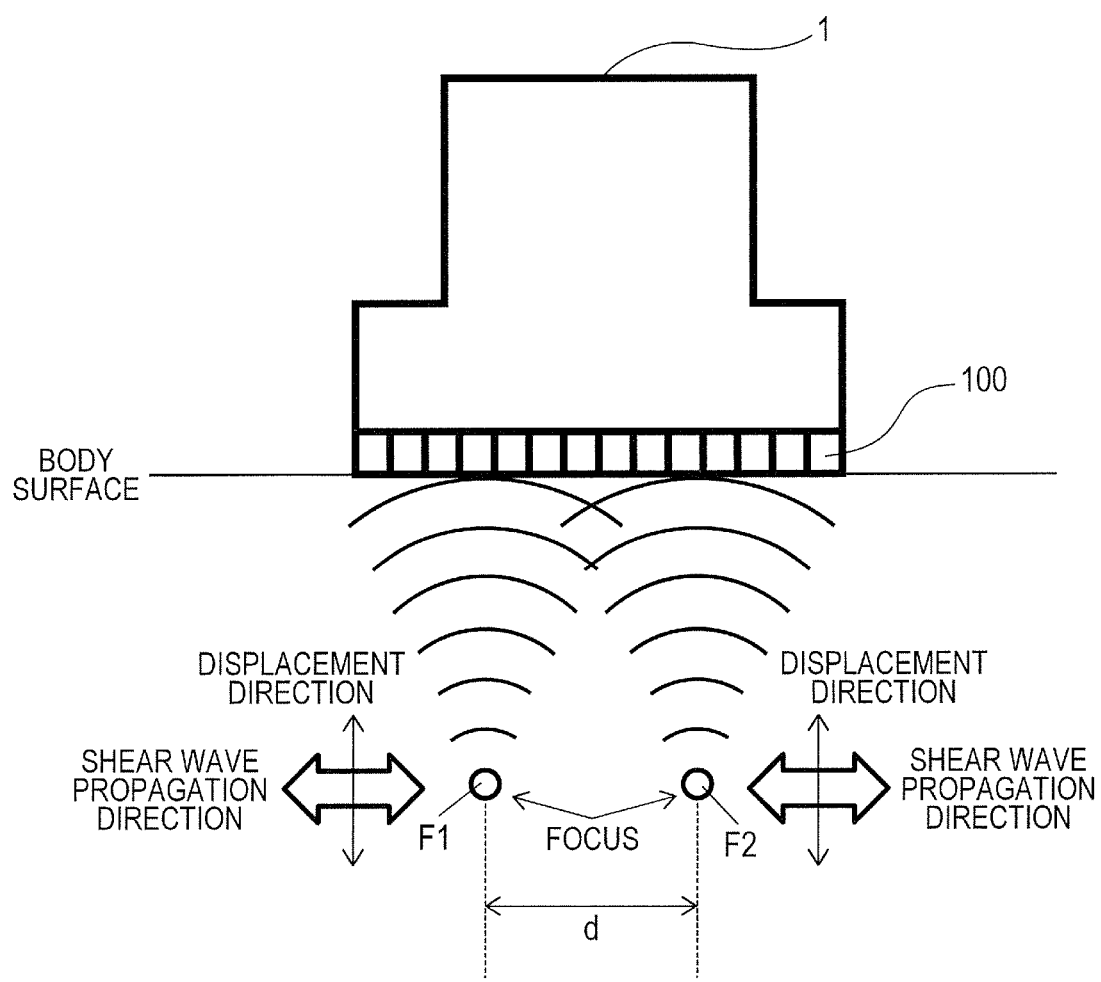
FIG. 15 shows measurement by an ultrasound probe in the fifth embodiment.

In FIG. 15, distance between the two focuses shall be d. As a value of d gets smaller, that is, as distance between the focus F1 and the focus F2 is reduced, a degree of interference increases. However, when the distance between the focuses is reduced, the rise E of temperature between the focuses becomes greater than temperature at the focus by heat conduction and safety is deteriorated. Conversely, as "d" is increased, the rise of temperature is inhibited and safety is enhanced, however, a degree of interference gets small. Accordingly, an optimum value of d is a value at which a maximum value of the rise of temperature is similar to a maximum value of the rise of temperature at each focus and the interference of a wave is caused. Accordingly, the optimum value d depends upon the depth of the focus, the irradiation time of the transmission beam for generating displacement, a frequency, a diagnosed part and others.

The diagnosed part has an effect on sonic velocity, the absorption of ultrasound, thermal conductivity and others respectively in a living body. For example, in the case of a liver, a range of d is $10\lambda < d < 30\lambda$ and in the case of a mammary gland, a range of d is $5\lambda < d < 30\lambda$.

The value d is read from a memory not shown by a central control unit 3 and is set in a focal position setting device 12. Further, a value related to the switching cycle is determined based upon the set value of d and estimated values of the velocity of shear waves.

As described above, in this embodiment, shear waves generated at the two focuses interfere, changing the switching cycle, a switching cycle when an amplitude gets great is calculated, and the heterogeneity of sonic velocity that proceeds from structure is detected. A condition on which an interference wave is amplified will be described below.

Figure 17A:
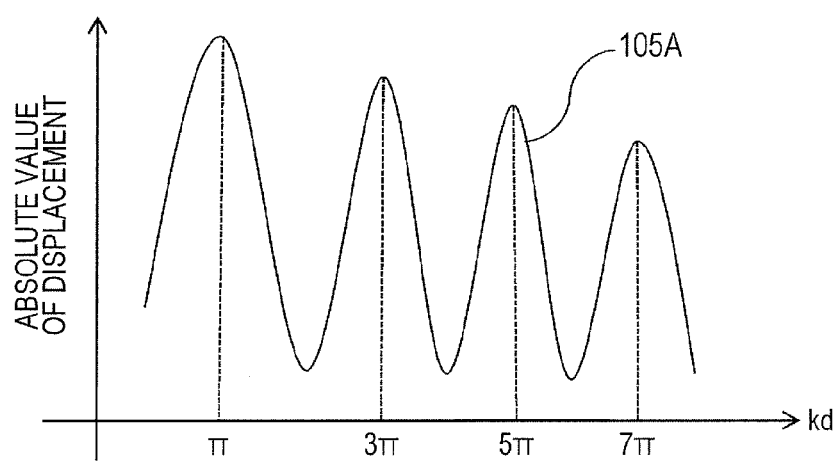
FIG. 17A shows the spectral distribution of the displacement of a shear wave in the case of a tissue the sonic velocity of which is uniform in the fifth embodiment.

First, a case that sonic velocity that proceeds from structure is homogeneous will be described. An inverse number of the switching cycle Tm is represented as a switching frequency (a repetition frequency) fm and fm shall be 1/Tm. In this case, a condition on which an interference wave is amplified and an absolute value of displacement becomes a peak value (a maximal value) is a case that distance d between the two focuses is equivalent to $(n+\frac{1}{2})$ times of a wavelength $\lambda$, the condition can be expressed by a mathematical expression 2, and is shown in a waveform 105A in FIG. 17A. The switching frequency fm at this time is expressed as fM (n).

$$k*d=(2\pi fM(n)/c)*d=2\pi(n+\frac{1}{2}) \tag{2}$$

However, k denotes a wave number ($=2\pi/\lambda$), c denotes the velocity of a shear wave and n denotes 0 or a positive integer (n=0, 1, 2, - - - ).

As TM (n) is 1/fM (n) when a value to be the peak value of the switching cycle Tm is TM (n), a mathematical expression 3 is derived from the mathematical expression 2.

$$TM(n)=d/c*(2/(2n+1)) \tag{3}$$

For example, in a case that n is 1 and d is 2 [mm], TM (1) is 1.3 [ms](fM (1)=750 [Hz]) when c is 1 [m/s], TM (1) is 1.1 [ms] (fM (1)=900 [Hz]) when c is 1.2 [m/s]. The velocity c of the shear wave can be calculated based upon a value of $\Delta$ (n) and distance d between the two focuses. It is desirable that Tm which is the switching cycle for turning on/off the transmission beam for generating displacement is controlled in a range of a few Hz to a few kHz. Besides, this art has a characteristic that heterogeneity is detected according to not a cycle of a carrier signal of the transmission beam for generating displacement but the sequence control of turning on/off. Accordingly, beam width is narrowed by increasing a frequency of the carrier and imaging at high spatial resolution is enabled.

Next, a case that sonic velocity that proceeds from structure is heterogeneous will be described. For example, a case that the shear wave passes a medium having two different sonic velocity will be described below.

Figure 17B:
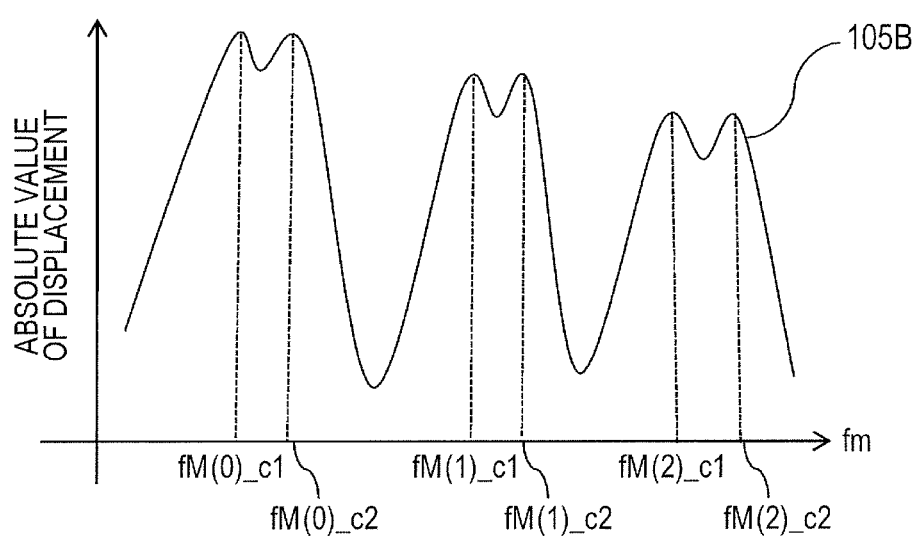
FIG. 17B shows the spectral distribution of the displacement of a shear wave in the case of a tissue the sonic velocity of which is heterogeneous in the fifth embodiment.

As shown in FIG. 17B, in a graph showing relation between an absolute value of the displacement of the shear wave and fm, a peak corresponding to the sonic velocity c1 of the shear wave emerges at the time of "fM (n)_c1" and besides, a peak corresponding to the sonic velocity c2 of the shear wave exists at the time of "fM (n)_c2". When c2>c1 and fM(n+1)_c1>fM(n+1)_c2, heterogeneity can be detected. In the heterogeneity detecting device 26, the width of spectral distribution for example is calculated as a parameter of heterogeneity equivalent to the width of the temporal waveform in the first to fourth embodiments. In the calculation of the width of spectral distribution, an absolute value of displacement is calculated by dividing a value integrated in a direction of fm by a peak value of the absolute value of displacement.

The above-mentioned method can be also applied to a case that different two or more sonic velocities exist.

In the hardness spectrum calculating device 28 shown in FIG. 14, spectrum analysis is applied to an output signal from the detecting device 25 and spectrum information is output to the heterogeneity detecting device 26.

Figure 19:
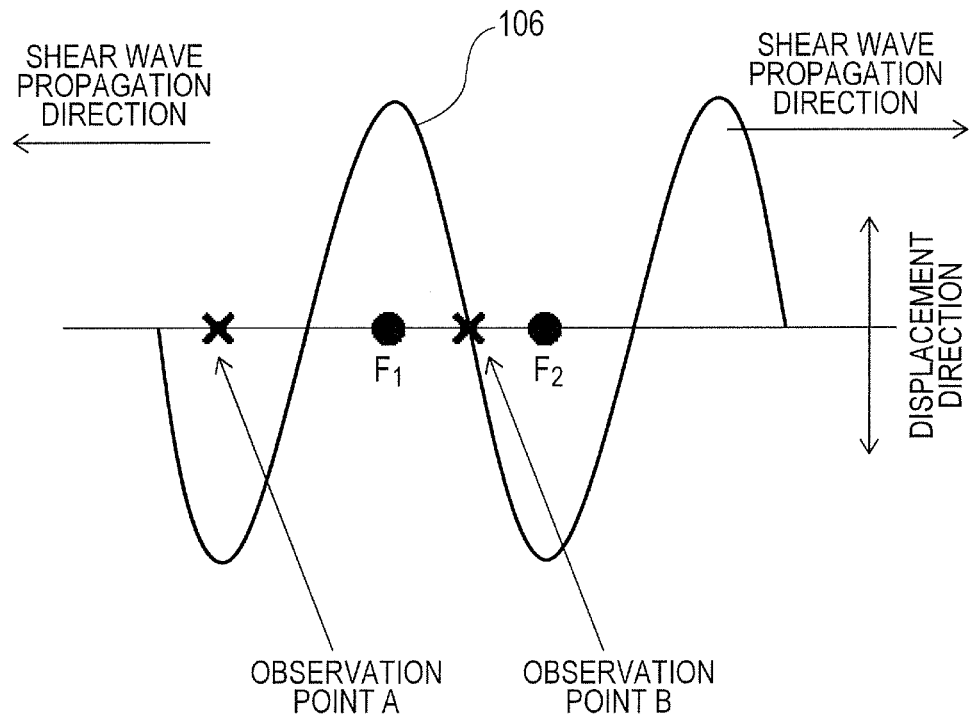
FIG. 19 is an explanatory drawing for explaining a direction of displacement and a direction of the propagation of a shear wave in the fifth embodiment.

A displacement detection point is set to a location such as an observation point A of a waveform 106 shown in FIG. 19 and a location such as an observation point B in which displacement is minimum is required to be possibly avoided. When a transient phenomenon such as the radiation of the transmission beam for generating displacement is turned on only once is observed, this consideration is not important so much. However, as a maximal value and a minimal value of the absolute value (=an amplitude value) of displacement alternately emerge when the interference of the shear waves having the two focuses as a sound source is used, a location in which the absolute value of displacement is estimated to be the maximal point on a raster for monitoring displacement is selected or plural monitoring points are set, and such a device that the maximal point is included in the observation point is made. When the plural monitoring points are set, a differential value between an absolute value of displacement at the maximal point and an absolute value of displacement at the minimal point may be also regarded as an amount of displacement.

Figure 18:
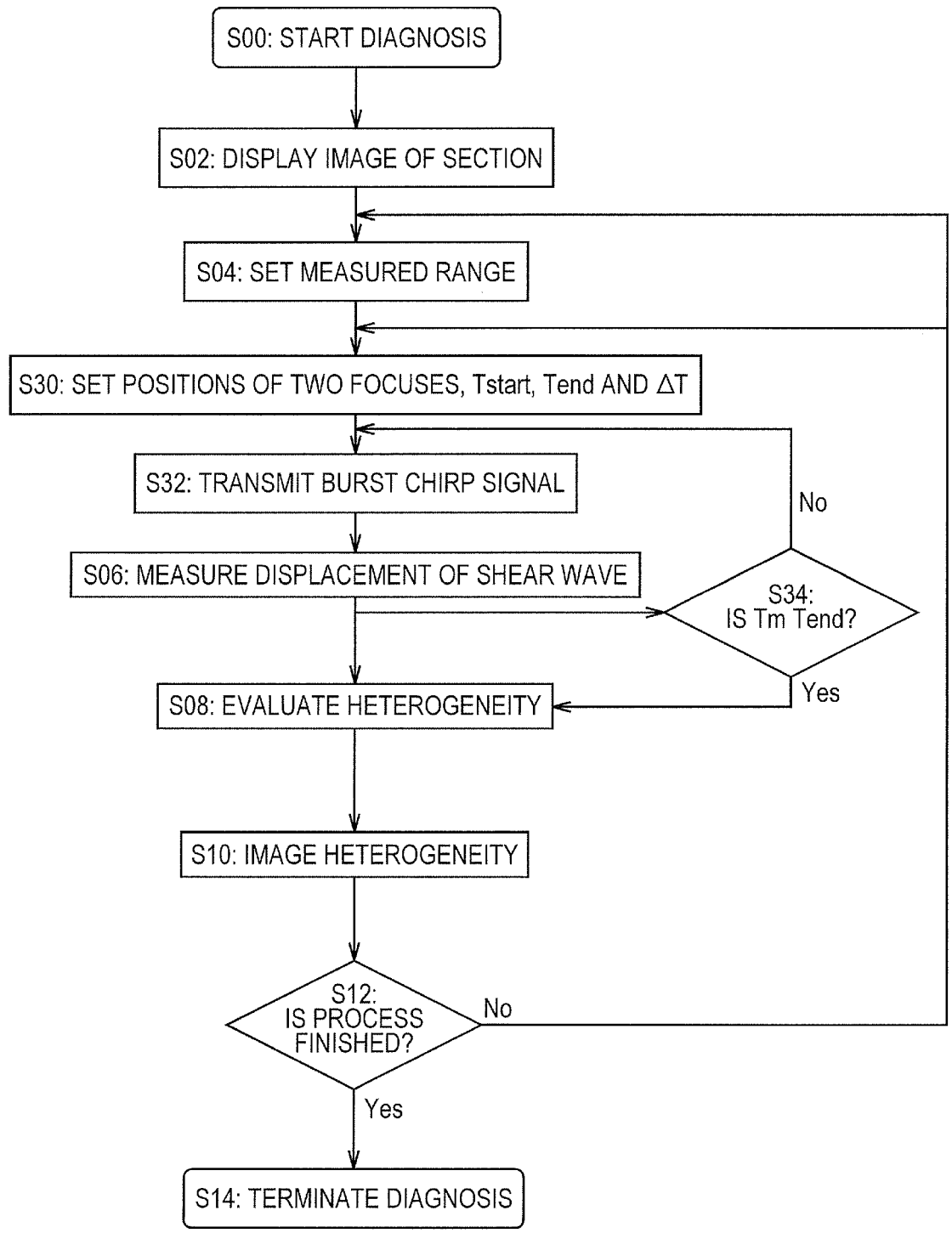
FIG. 18 is a flowchart showing the measurement of heterogeneity utilizing a burst chirp mode in the fifth embodiment.

FIG. 18 is a flowchart showing the diagnosis of heterogeneity of sonic velocity that proceeds from structure by the burst chirp mode in this embodiment. As steps S00 to S04, S12 and S14 are the same as those in the flowchart in measuring heterogeneity in the first embodiment, the description is omitted.

In S30, positions of the two focuses F1, F2, an initial value Tstart and a final value Tend respectively of the switching cycle in the radiation onto the two focuses of the transmission beam for generating displacement and an interval ΔT are set.

As for the positions of the two focuses, for example, a central point of the two focuses (the center of a straight line tying the two focuses of each set in this case) is set as a point of interest (POI) and distance between the two focuses is set. The POI can be also set using an input device such as a keyboard, a mouse and a touch screen respectively not shown by an operator with the operator watching the image displayed in the step S02 and besides, an estimated value calculated based upon a luminance value of the displayed image, a contour of a tissue and others may be also automatically set in the focal position setting device 12. When an operator manually sets POI, he/she can set a focus, avoiding a blood vessel and others. As described above, distance between the two focuses has a value smaller than distance in which two shear waves interfere with each others and larger than the width of the transmission beam for generating displacement radiated onto each focus. When an operator determines focal positions, the above-mentioned optimum value of the distance d or a maximum value and a minimum value of optimum distance d is/are displayed on a screen and the operator determines the positions based upon these. When the distance is set, a value of n in the mathematical expression 3 and optimum observation points are determined based upon estimated velocity of the shear waves. The observation point is determined based upon a maximal point of an absolute value of the displacement of the shear wave or plural positions including the maximal point in the propagational distance of the shear wave. The observation point is automatically set or is set via the input device by the operator. A raster used for the detection of an amplitude (a few μm to a few tens μm) of shear wave propagation on the observation point and a sampling point on the raster are determined. In each raster, PRF (a frequency of pulses repeatedly transmitted) of the reception of a beam for detecting displacement is set so that Nyquist's theorem is met for an estimated frequency of the shear wave. For example, when the raster is the same as a direction of the displacement of the shear wave, the PRF is set to double or more times of the frequency of the shear wave. Determined "n" and the observation point may be also displayed on the screen. The initial value Tstart and the final value Tend are set to values at which a peak is acquired in a range where the mathematical expression 3 is met for a measured part and the distance d between the two focuses. These set values may be also automatically set according to the measured part, depth and the distance between the focuses and the operator may also set them using the input device.

Next, in a step S32, after a reference signal used for correlation operation performed when the displacement of the shear wave is detected is acquired, a burst chirp signal is transmitted at the switching cycle of T1 (=Tstart) and the shear wave is generated at the two focuses.

In a step S06, the beam for detecting displacement for observing the shear waves is transmitted and received. The detection of displacement at each observation point may be also ordinarily performed since the burst chirp signal is turned off until the shear waves reach all observation points and pass them or time since the shear waves reach until they pass is calculated based upon distance between the focus and the observation point and the estimated velocity of the shear wave beforehand and the detection may be also performed only for the time. As in the latter method, the PRF can be increased, the high-precision detection of displacement is enabled. After a signal equivalent to fm is extracted from a received signal in signal processing such as a band-pass filter in the detecting device 25, well-known correlation operation and others are performed and the displacement of the shear waves is calculated. The correlation operation is performed using the reference signal and an echo signal every time received by the beam for detecting displacement. A temporal waveform of an amplitude of the shear wave at each observation point is acquired by the operation.

In a step S34, it is determined whether the switching cycle Tm immediately before is Tend or not. When the switching cycle is not Tend, control is returned to the step S32 and a burst chirp signal is transmitted at a switching cycle of next (Tm+1). When a reference signal is acquired again in the step S32, the robustness of correlation operation by the displacement of the focal position during measurement increases. Besides, as for the transmission of a burst chirp signal after the switching cycle of (Tm+1), the acquisition of a reference signal is omitted and if correlation operation is executed using the first acquired reference signal, measurement time can be reduced.

In the case of Tend, in a step S08 shown in FIG. 18, the evaluation of heterogeneity is performed. Spectrum information output from the hardness spectrum calculating device 28 may be also output to the heterogeneity detecting device 26 every time the displacement of the shear wave is measured in the step S06 and after determination as Tend in a step S34, the spectrum information may be also output to the heterogeneity detecting device 26 together after the measurement of displacement is made at all Tm. As described above, an evaluation value of heterogeneity is equivalent to the width of spectral distribution calculated in the heterogeneity detecting device 26. In a step S10 shown in FIG. 18, a value showing measured heterogeneity, for example, the width of spectral distribution is displayed on the screen of a display 5 together with an image of a section.

Figure 20:
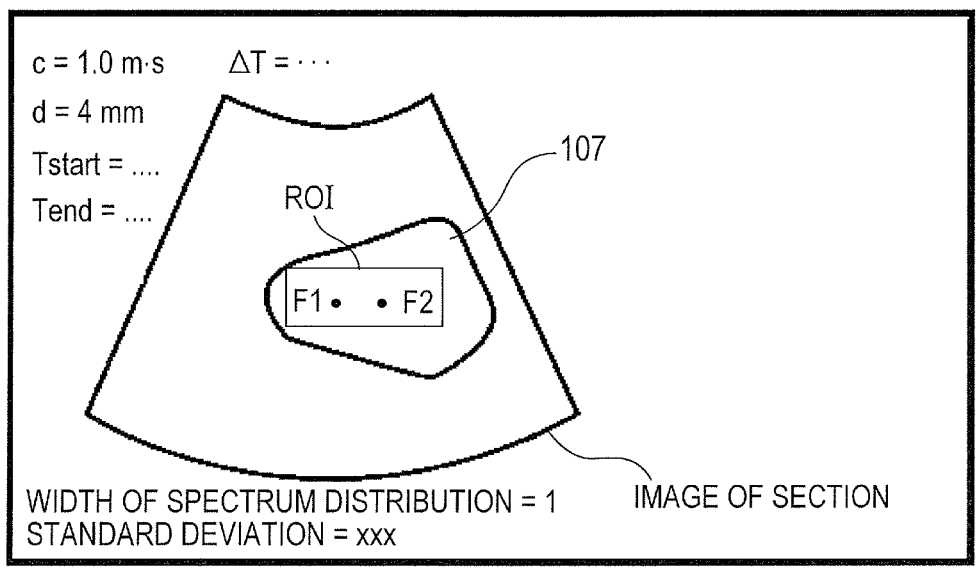
FIG. 20 is an explanatory drawing for explaining an example of a screen that displays heterogeneity in the fifth embodiment.

As shown in FIG. 20, a result of calculation is displayed as a numeric value on the same screen as the image of the section 107. Besides, the positions F1, F2 of the two focuses and the distance d may be also displayed with them superimposed on the image of the section 107 and they may be also displayed on the screen together with the initial value Tstart and the final value Tend of the switching cycle in the radiation of the transmission beam for generating displacement and the interval ΔT. Hereby, the operator watches the displayed image and graph, changes a measurement parameter such as the positions of the two focuses, the distance d, the initial value Tstart and the final value Tend of the switching cycle and the interval ΔT, and can measure again. Though not shown, as shown in the middle figure in FIG. 9 in the first embodiment, the width of spectral distribution is displayed in color in ROI in another display method. At that time, a color bar corresponding to the width of spectral distribution is displayed on the same screen and the operator can visually judge a degree of the heterogeneity of the measured part. In the color bar, a scaling value corresponding to the measured part is read from a storage not shown and others via the central control unit 3 beforehand and the color bar is scaled. Besides, a space derivative related to the propagation x of the shear wave for the width D_S of spectral distribution in each position x (n), that is, dD_S/dx is calculated and the information of the width of spatial spectral distribution can be also mapped in ROI. On the screen at that time, a color map representing the space derivative of the width of spectral distribution and the color bar corresponding to the space derivative of the width of spectral distribution are displayed in ROI. Heterogeneity having higher spatial resolution can be diagnosed by displaying a value of the space derivative. Variations of the method of detecting the heterogeneity of sonic velocity that proceeds from structure by the burst chirp mode will be described below.

Control is made so that turning on/off the transmission beam for generating displacement toward the two focuses are alternate, however, control is made so that turning on/off the beam toward the two focuses is simultaneous and displacement can be also generated at the same time. In this case, as interference waves are amplified and a peak emerges when d is equivalent to (n+1) times of a wavelength λ, a mathematical expression 4 is acquired corresponding to the mathematical expression 2.

$$k*d=(2\pi f/c)*d=2\pi(n+1) \quad (4)$$

For a high-precision measurement method of the heterogeneity of sonic velocity, the interval ΔT of the switching cycle is roughly set at the first time, measurement is made, TM is calculated, in the next measurement, the interval ΔT of the switching cycle in the vicinity of TM is set to a stricter value, and a more detailed value of TM may be also calculated. Stricter difference in velocity can be detected by more strictly setting a value of the interval ΔT of the switching cycle as described above and the high-precision evaluation of the heterogeneity of sonic velocity is enabled.

Besides, after on-off control over the same Tm is repeated several times without changing each switching cycle Tm to the next switching cycle T (m+1) by one on-off control, each switching cycle may be also set to the next switching cycle. More sensitive measurement is enabled by repeating on-off control over the same Tm several times.

A value of Tm is varied from a larger value to a smaller value, however, conversely, the value can be also varied from a smaller value to a larger value and ΔTm can be also varied based upon a certain function such as geometrical series except a fixed value.

Further, the method of measuring the heterogeneity of sonic velocity based upon a peak value (a maximal value) is described above, however, a minimal value may be also used. In that case, in the waveform 105A shown in FIG. 17, kd has values of 2π, 3π, - - - .

Furthermore, the method of radiating the transmission beam for generating displacement onto the two focuses is described above, however, two or more (for example, four) focuses are set at an equal interval on one line in a living body and the transmission beam for generating displacement can be also radiated onto every other focus in the same sequence as the focus F1 or the focus F2 (for example, the sequence of the focus F1, the sequence of the focus F2, the sequence of the focus F1 and the sequence of the focus F2 respectively shown in FIG. 17 sequentially from an end for the four focuses).

Furthermore, a method of fixing a switching cycle, varying distance d between focuses and measuring is also conceivable. In this method, as a position in which the transmission beam for generating displacement is focused can be changed, the rise of temperature in a living body is decreased and safe measurement is enabled.

Furthermore, the radiation of the transmission beam for generating displacement and the transmission/reception of the beam for detecting displacement can be also finished only once by using a random wave including plural switching frequencies fm in place of switching a burst switching frequency fm and transmitting the beam. Spectral analysis is made after the calculation of the displacement of the shear wave and displacement for the plural switching frequencies fm is calculated. Hereby, measurement time can be reduced.

The case that the burst chirp mode is applied for the method of evaluating the heterogeneity of sonic velocity that proceeds from tissue structure has been described. The burst chirp mode can be also applied when it is determined that the heterogeneity of sonic velocity that proceeds from tissue structure exists and concrete shear wave velocity is estimated. For example, suppose that structures having two different shear wave velocity exist in measured ROI and shear wave velocity c1, c2 is estimated using the parameters calculated in the mathematical expression 1 in the second embodiment. At that time, to acquire higher-precision measurement, the burst chirp mode is applied. First, TM1 and TM2 corresponding to the shear wave velocity c1 and c2 are calculated in the mathematical expression 3. Next, more precise shear wave velocity c1, c2 can be measured by setting strict ΔT also based upon switching frequencies in the vicinity of TM and calculating a more detailed value of TM. The shear wave velocity c1, c2 can be also estimated based upon fM (n)_c1 and fM (n)_c2 in this embodiment in addition to estimating the shear wave velocity in the mathematical expression 1 in the second embodiment.

As in the second embodiment, as to a waveform after fitting and noise removing processing are applied to an absolute value of displacement, parameters related to half-width, an amplitude value and fm are calculated and heterogeneity may be also evaluated using a value acquired by calculating using these parameters or plural parameters, an arbitrary threshold and others.

When the heterogeneity of sonic velocity that proceeds from frequency dispersion is evaluated at repetition frequencies PRFp (1) and PRFp (2) in the radiation of the two different transmission beams for generating displacement, the width of spectral distribution can be similarly calculated based upon relation between the absolute value of displacement and fm. Further, the above-mentioned method may be also applied to the evaluation of heterogeneity that proceeds from amplitude.

In the embodiments of the present invention, the following two types of ultrasound diagnosis apparatuses have been described in detail. The first type is the ultrasound diagnosis apparatus which is provided with the ultrasound probe that transmits/receives an echo signal from a subject, the displacement generating unit that radiates the ultrasonic focused beam onto the subject so as to displace a tissue and the displacement detecting unit that receives the echo signal from the subject and detects a temporal waveform of the displacement of the shear wave generated by the ultrasonic focused beam in plural positions and in which the displacement detecting unit is provided with the heterogeneity detecting device that evaluates the heterogeneity of the subject based upon the temporal waveform of the displacement of the detected shear wave. The second type is the ultrasound diagnosis apparatus which is based upon the ultrasound diagnosis apparatus that diagnoses a subject by ultrasound, which is provided with the ultrasound probe that transmits/receives an echo signal from the subject, the displacement generating unit that radiates the ultrasonic focused beam onto the subject so as to displace a tissue and the displacement detecting unit that receives an echo signal from the subject and detects a temporal waveform of the displacement of the shear wave generated by the ultrasonic focused beam in plural positions and in which the displacement generating unit is provided with the transmission beam generating device for generating displacement that generates the ultrasonic focused beam and the beam frequency setting device that sets a frequency of the ultrasonic focused beam and the displacement detecting unit is provided with the heterogeneity detecting device that evaluates the heterogeneity of the subject based upon the detected displacement of the shear wave.

In the above-mentioned all embodiments, when the shear wave is generated, a well-known method such as mechanical driving (a DC motor, a vibrating pump and others), manual pressure, pressure by an electric pulse and the movement of a blood vessel, a heart and others may be also used in place of the transmission beam for generating displacement.

Besides, it is described above that the width in a propagation direction of the shear wave (in this case, the width in an azimuth) is determined based upon the effective propagation distance of the shear wave in the dimension of ROI set in the step S04. Moreover, it is described above that the vertical width (in this case, the width in a direction of depth) in the propagation direction of the shear wave of measured ROI is determined based upon the width of a sound source in a direction in which the transmission beam for generating displacement is propagated, for example, in the direction of depth in a body in FIG. 2. For a method of setting the dimension of another ROI, heterogeneity in the ROI can be also detected, scanning by setting the dimension of the ROI to be larger than the dimension described in the step S04 and generating the shear wave, shifting a position which the transmission beam for generating displacement irradiates.

In addition, a two-dimensional probe may be also used in place of the linear array type probe. Further, a well-known piezo-electric element and a well-known electrostatic element made of a ceramic, polymeric materials, silicon and others for example are used for each element of the ultrasound probe 1.

Furthermore, a virtual plane wave of the shear wave is generated by radiating the plural transmission beams for generating displacement in the propagation direction and effective propagation distance can be also extended.

Furthermore, a part different from a peripheral tissue in a degree of homogeneity is extracted by image processing based upon pixel information (a luminance value and others) of an image showing heterogeneity in an image of a section displayed on the display 5 in an image processing unit not shown and the part estimated to be a lesion tissue (a tumor) may be also displayed on the screen. For the extraction of the part different from the peripheral tissue in the degree of homogeneity, in addition to using an image displayed on the display 5, quantity showing heterogeneity calculated in the heterogeneity detecting device 26 can be also extracted by signal processing in the heterogeneity detecting device. A location judged as the lesion tissue may be further also analyzed using the existing diagnostic function test (Doppler method) and others.

For a measuring object in the above-mentioned various embodiments, a liver, a mammary gland, a blood vessel and a prostate can be given for example.

REFERENCE SIGNS LIST

1 - - - Ultrasound probe, 2 - - - Switch for switching transmission/reception, 3 - - - Central control unit, 4 - - - Digital scan converter, 5 - - - Display, 10 - - - Displacement generating unit, 11 - - - Transmission waveform generating device for generating displacement, 12 - - - Focal position setting device, 13 - - - Transmission beam generating device for generating displacement, 14 - - - Beam frequency setting device, 15 - - - Beam time setting device, 20 - - - Displacement detecting unit, 21 - - - Transmission waveform generating device for detecting displacement, 22 - - - Transmission beam generating device for detecting displacement, 23 - - - Received beam computing device for detecting displacement, 25 - - - Detecting device, 26 - - - Heterogeneity detecting device, 28 - - - Hardness spectrum calculating device, 100 - - - Each element of ultrasound probe 1.

The invention claimed is:

1. An ultrasound diagnosis apparatus, comprising:
an ultrasound probe that receives and transmits an echo signal from an inside of a subject;
a displacement generating unit that radiates an ultrasonic focused beam to the inside of the subject so as to displace a tissue; and
a displacement detecting unit that receives the echo signal and detects a temporal waveform of a displacement of a shear wave generated by the ultrasonic focused beam in a plurality of positions,
wherein the displacement detecting unit is provided with a heterogeneity detecting device that evaluates a heterogeneity of the subject based upon the temporal waveform, and
wherein the heterogeneity detecting device acquires at least two types of information from the temporal waveform, calculates a width of the temporal waveform based upon the at least two types of information, and evaluates the heterogeneity.

2. The ultrasound diagnosis apparatus of claim 1, wherein the heterogeneity is a heterogeneity of a sonic velocity of the shear wave that proceeds from a structure of the subject.

3. The ultrasound diagnosis apparatus of claim 1, wherein the heterogeneity is a heterogeneity of a sonic velocity of the shear wave that proceeds from a frequency dispersion.

4. The ultrasound diagnosis apparatus of claim 1, wherein the at least two types of informations are an integrated value and a maximum amplitude value respectively of the temporal waveform.

5. The ultrasound diagnosis apparatus of claim 1, wherein the at least two types of informations are a half-width and a maximum amplitude value respectively of the temporal waveform.

6. The ultrasound diagnosis apparatus of claim 1, wherein the heterogeneity detecting device calculates a number of peaks of the shear wave and evaluates the heterogeneity.

7. The ultrasound diagnosis apparatus of claim 1, wherein the heterogeneity detecting device performs space differential operation for the displacement of the shear wave.

8. The ultrasound diagnosis apparatus of claim 1, wherein the displacement generating unit is provided with a focal position setting device that sets a focal point of the ultrasonic focused beam.

9. The ultrasound diagnosis apparatus of claim 8, wherein: the focal position setting device sets a focal point of the ultrasonic focused beam in different positions in the subject.

* * * * *